(12) United States Patent
Yao et al.

(10) Patent No.: US 8,738,149 B2
(45) Date of Patent: May 27, 2014

(54) FLEXIBLE CIRCUIT ELECTRODE ARRAY DEVICE AND A METHOD FOR BACKSIDE PROCESSING OF A FLEXIBLE CIRCUIT ELECTRODE DEVICE

(75) Inventors: Qingfang Yao, Valencia, CA (US); Jordan Matthew Nevsmith, Pasadena, CA (US); Neil Hamilton Talbot, Crescenta, CA (US); James Singleton Little, Saugus, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 49 days.

(21) Appl. No.: 13/397,604

(22) Filed: Feb. 15, 2012

(65) Prior Publication Data
US 2012/0150270 A1    Jun. 14, 2012

Related U.S. Application Data

(62) Division of application No. 12/177,038, filed on Jul. 21, 2008, now Pat. No. 8,145,322.

(60) Provisional application No. 60/950,754, filed on Jul. 19, 2007, provisional application No. 60/971,173, filed on Sep. 10, 2007.

(51) Int. Cl.
*A61N 1/04* (2006.01)

(52) U.S. Cl.
USPC .................. 607/115; 607/54; 607/2

(58) Field of Classification Search
USPC .......... 607/2, 54, 115–119; 427/2.24; 29/829, 29/842, 846
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,750,926 A * | 5/1998 | Schulman et al. | 174/564 |
| 5,935,155 A | 8/1999 | Humayun et al. | |
| 6,400,989 B1 | 6/2002 | Eckmiller | |
| 6,458,157 B1 | 10/2002 | Suaning | |
| 7,877,866 B1 * | 2/2011 | Greenberg et al. | 29/829 |

\* cited by examiner

*Primary Examiner* — Brian T Gedeon
(74) *Attorney, Agent, or Firm* — Scott B. Dunbar; Gary Schnittgrund

(57) ABSTRACT

The invention involves a flexible circuit electrode array device comprising: a polymer layer; wherein the polymer layer includes one or more metal traces, an electrode array; one or more bond pads; and the electrode array is located on the opposite side of the polymer layer.

The invention further involves a method for backside processing of a flexible circuit electrode device, comprising: applying polymer film on a substrate; processing the front side; releasing the polymer film from substrate; flipping over the polymer film and fixing it onto the substrate; processing the backside; and final releasing of the polymer film from the substrate.

The invention further involves a method for backside processing of a flexible circuit electrode device, comprising: processing the front side without releasing the polymer; processing the backside by sacrificial substrate method, or by laser drilling method; and releasing the polymer film from the substrate.

14 Claims, 23 Drawing Sheets

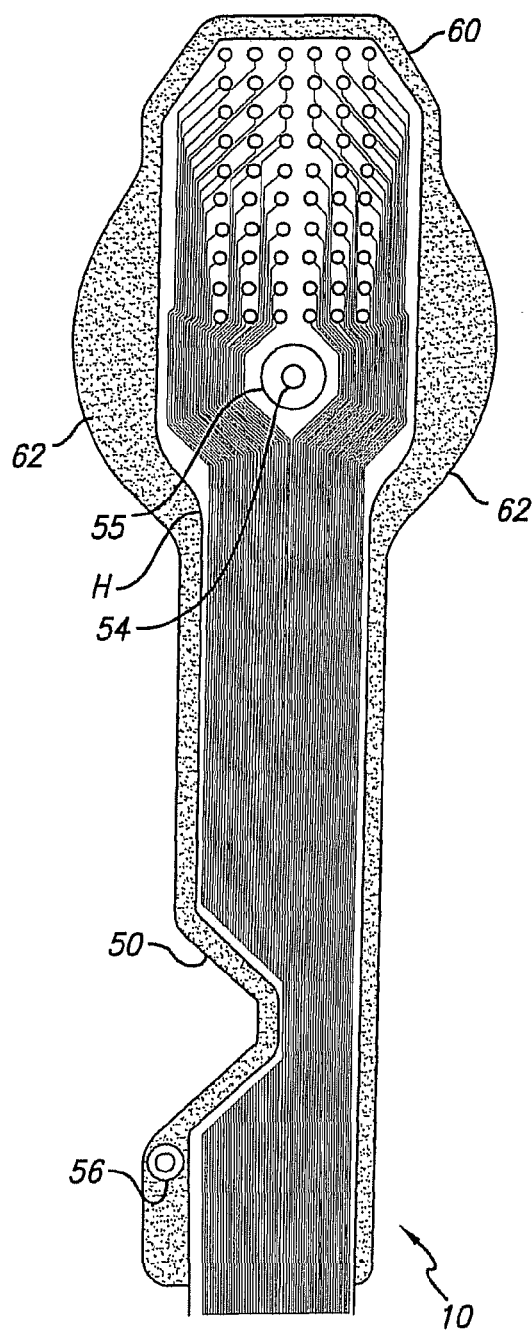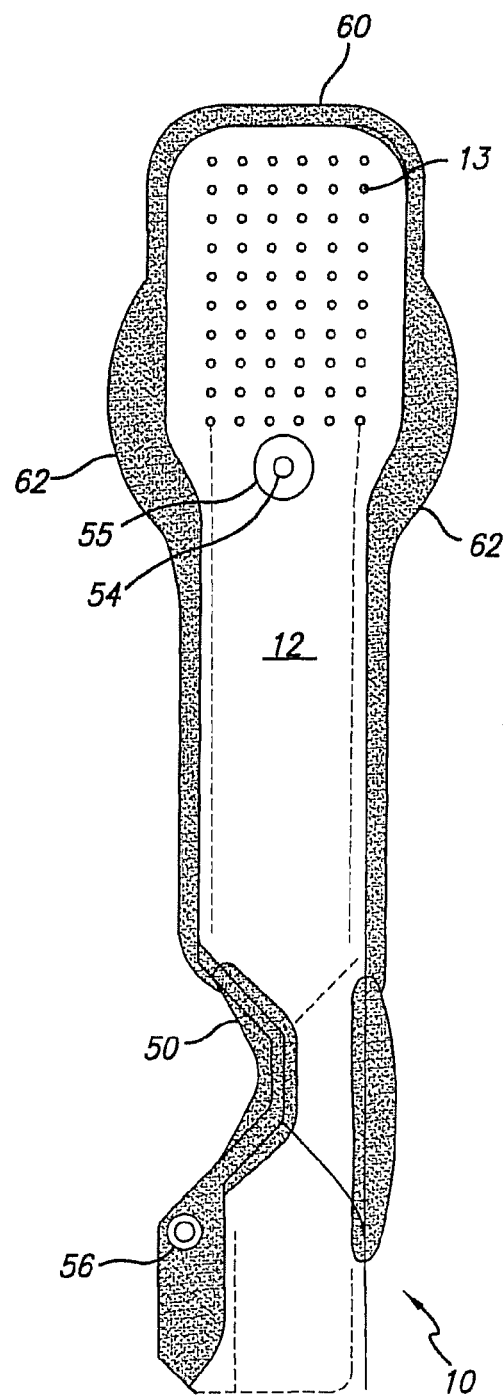

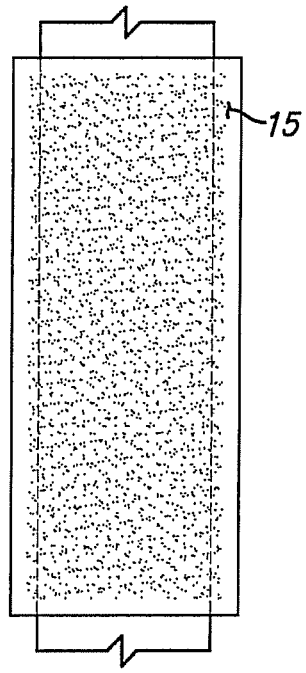 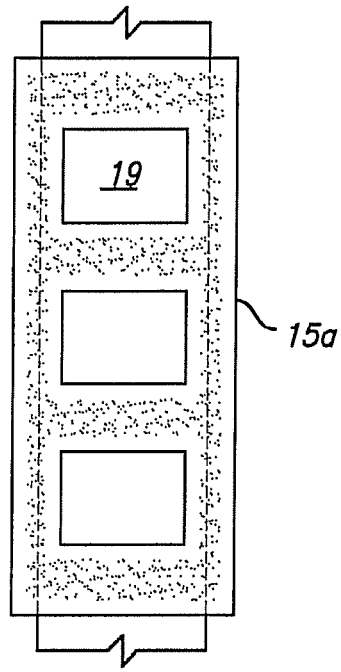 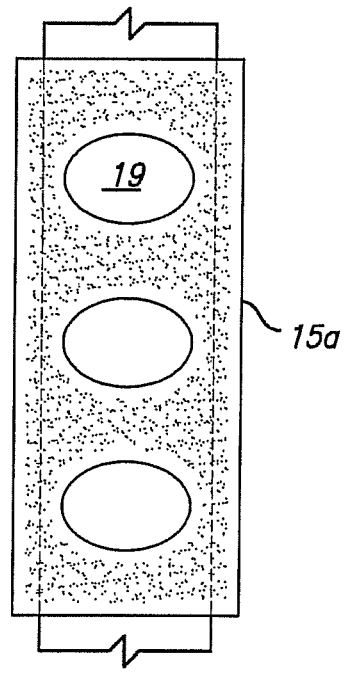
FIG. 31        FIG. 32        FIG. 33
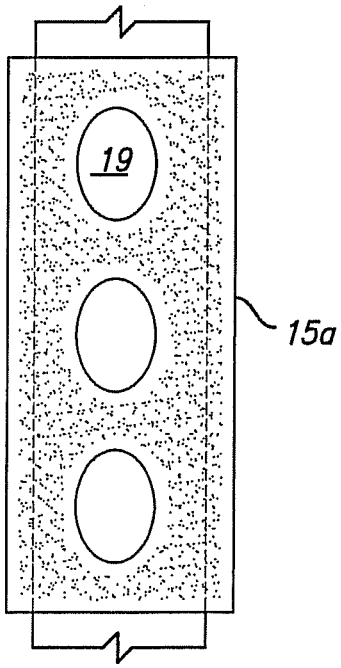 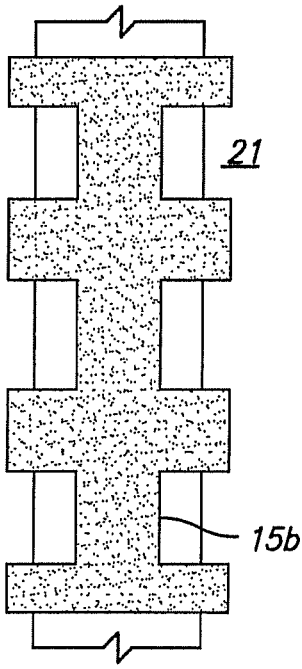 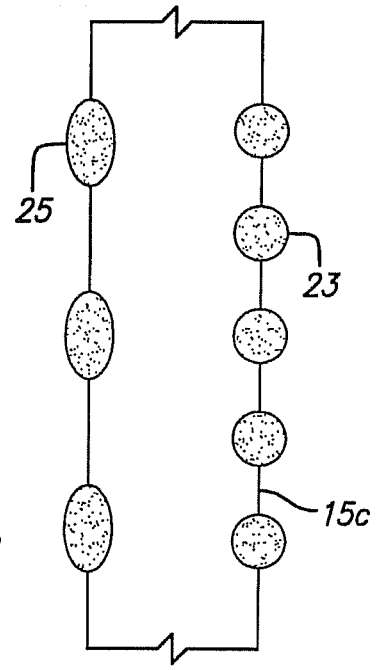
FIG. 34        FIG. 35        FIG. 36

FLEXIBLE CIRCUIT ELECTRODE ARRAY DEVICE AND A METHOD FOR BACKSIDE PROCESSING OF A FLEXIBLE CIRCUIT ELECTRODE DEVICE

CROSS-REFERENCE TO RELATED APPLICATIONS

This application is a divisional application of Ser. No. 12/177,038, filed Jul. 21, 2008, now issued as U.S. Pat. No. 8,145,322, for Flexible Circuit Electrode Array and a Method for Backside Processing of a Flexible Circuit Electrode Array, which claims the benefit of U.S. Provisional Application No. 60/950,754, Method for Backside Processing of a Polyimide Device, filed Jul. 19, 2007 and U.S. Provisional Application No. 60/971,173, "Method for Backside Processing of a Polyimide Device", filed Sep. 10, 2007, the disclosure of each is incorporated herein by reference.

GOVERNMENT RIGHTS NOTICE

This invention was made with government support under grant No. R24EY12893-01, awarded by the National Institutes of Health. The government has certain rights in the invention

FIELD OF THE INVENTION

The present invention is generally directed to neural stimulation and more specifically to an improved electrode array for neural stimulation. The present invention is more specifically directed to a method for backside processing of a flexible circuit electrode array device and an improved electrode array device achieved by the process of backside processing.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatus to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

Implanted stimulation devices usually stimulate the nerve or muscle tissue with biphasic electrical current pulses in either mono-polar or bipolar electrode configurations. In a bipolar configuration, the stimulating currents flow between two active electrodes or electrode groups which may be dynamically selected. In a mono-polar configuration, the stimulation currents flow in one phase from the active electrodes through the tissue being stimulated to the common electrode (CE), also called return electrode. The currents flow in the other phase in the reversed direction to balance the charge. In this case, the direction of the current flow is significantly affected by the relative placements or positioning of the active electrodes and the common electrode.

If an electrode array is placed on the surface of the tissue being stimulated without a ready method of confinement the array may not be in good contact with the retina tissue, or it drifts away from the retina. This applies especially for epi-retinal prosthesis where the stimulating electrode array is placed on the surface of the retina in the vitreous. If the return electrode is placed far away from the active electrode array, the current paths from the active stimulating electrodes will change because of the significant difference between the impedances of the retina tissue and of the vitreous and body fluids. As a result, there may not be enough current density passing through the neuronal cells in the retina tissue to cause a response, or the response may change when the array is moved.

In order to solve this problem, a large return electrode can be placed outside of the eyeball and directly under the active array. Thus the stimulating currents shall pass from the active electrodes through the tissue being stimulated. However, if the active electrodes are lifted from the tissue surface, the responses elicited by the stimulation of the individual electrodes may not be differentiable or distinctive because of the diffusive current paths from the lifted electrodes, resulting great reduction of effective resolution for percepts. Another possible method is to place the active electrode array underneath the retina while placing the return electrode in the vitreous. This sub-retina approach presents significant surgical difficultness when the device and array are implanted.

It is desired to a find a method for preparing a flexible circuit electrode array device which exposes conductors on both sides of the polymer device to meet special geometry requirements of the device.

SUMMARY OF THE INVENTION

The invention involves a flexible circuit electrode array device comprising a polymer layer; wherein the polymer layer includes one or more metal traces, an electrode array; one or more bond pads; and the electrode array is located on the opposite side of the polymer layer.

The invention further involves a method for backside processing of a flexible circuit electrode device, comprising: applying polymer film on a substrate; processing the front side; releasing the polymer film from substrate; flipping over the polymer film and fixing it onto the substrate; processing the backside; and final releasing of the polymer film from the substrate.

The invention further involves a method for backside processing of a flexible circuit electrode device, comprising: processing the front side without releasing the polymer; processing the backside by sacrificial substrate method, or by laser drilling method; and releasing the polymer film from the substrate.

The purpose of backside processing of a polyimide device is to expose conductors on the other side of the polyimide device so that conductors on both sides are opened to meet special geometry requirement of the device. Both sides of electrodes on an electrode array have to be open so that one side can be attached to retina and the other side to the bond pads of the electronic package. The advantage is that the device does not have to be folded when implanted because the electrode array is on the opposite side of the bond pads of the electronic package.

The invention involves several processes to achieve a flexible electrode array manufactured by a backside processing method. The approaches underlined are designed so that the proposed processes are to be compatible with current thin film electrode array thin film electrode array. The process can be implemented as a clean process without introducing any undesirable residue or hazardous material.

BRIEF DESCRIPTION OF THE DRAWINGS

FIG. 19 depicts a top view of a flexible circuit array and flexible circuit cable showing an additional horizontal angel between the flexible electrode array and the flexible cable.

FIG. 20 depicts another variation without the horizontal angel between the flexible electrode array and the flexible cable but with an orientation of the electrodes in the flexible electrode array as shown for the variation in FIG. 19.

FIGS. 31-36 show several surfaces to be applied on top of the cable.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
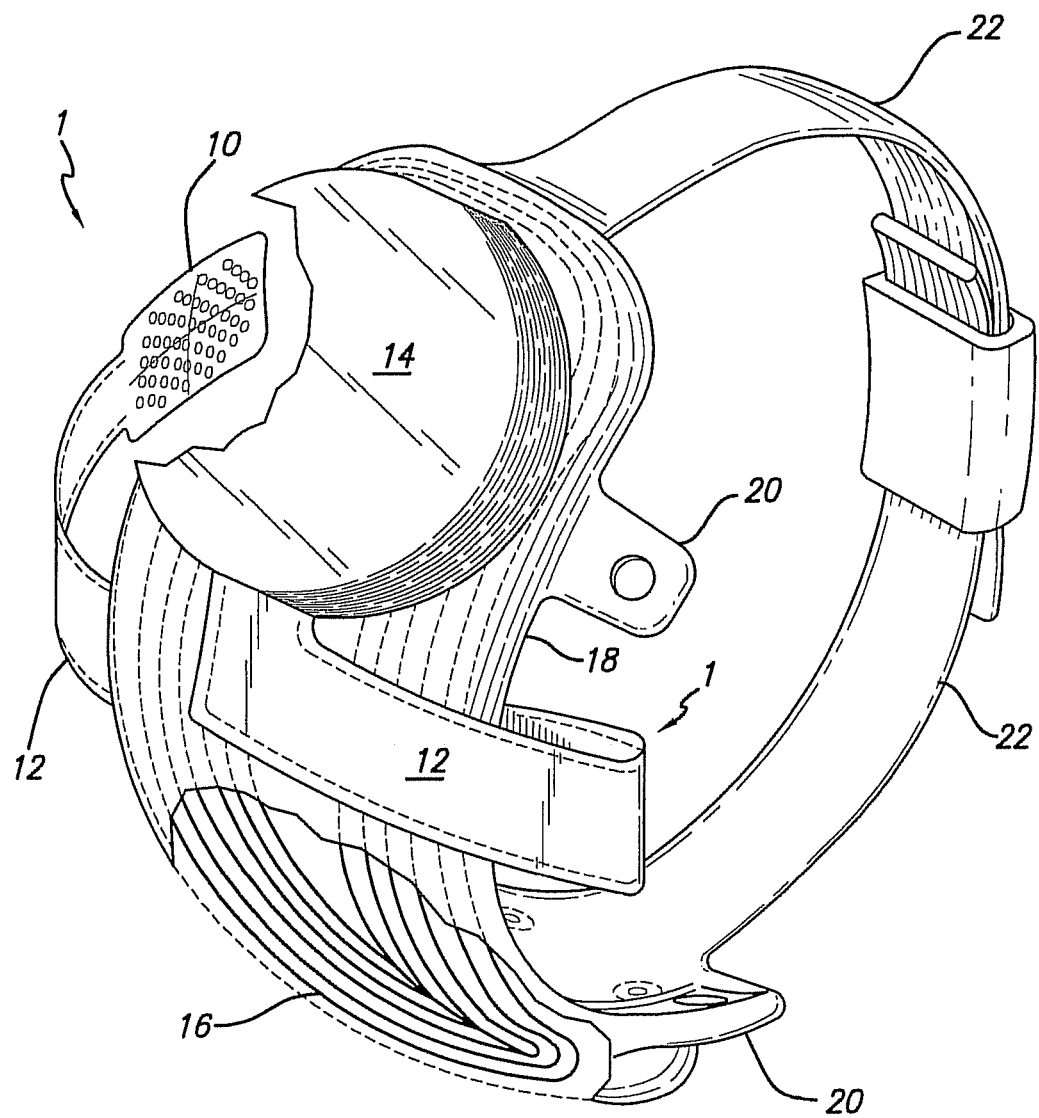
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
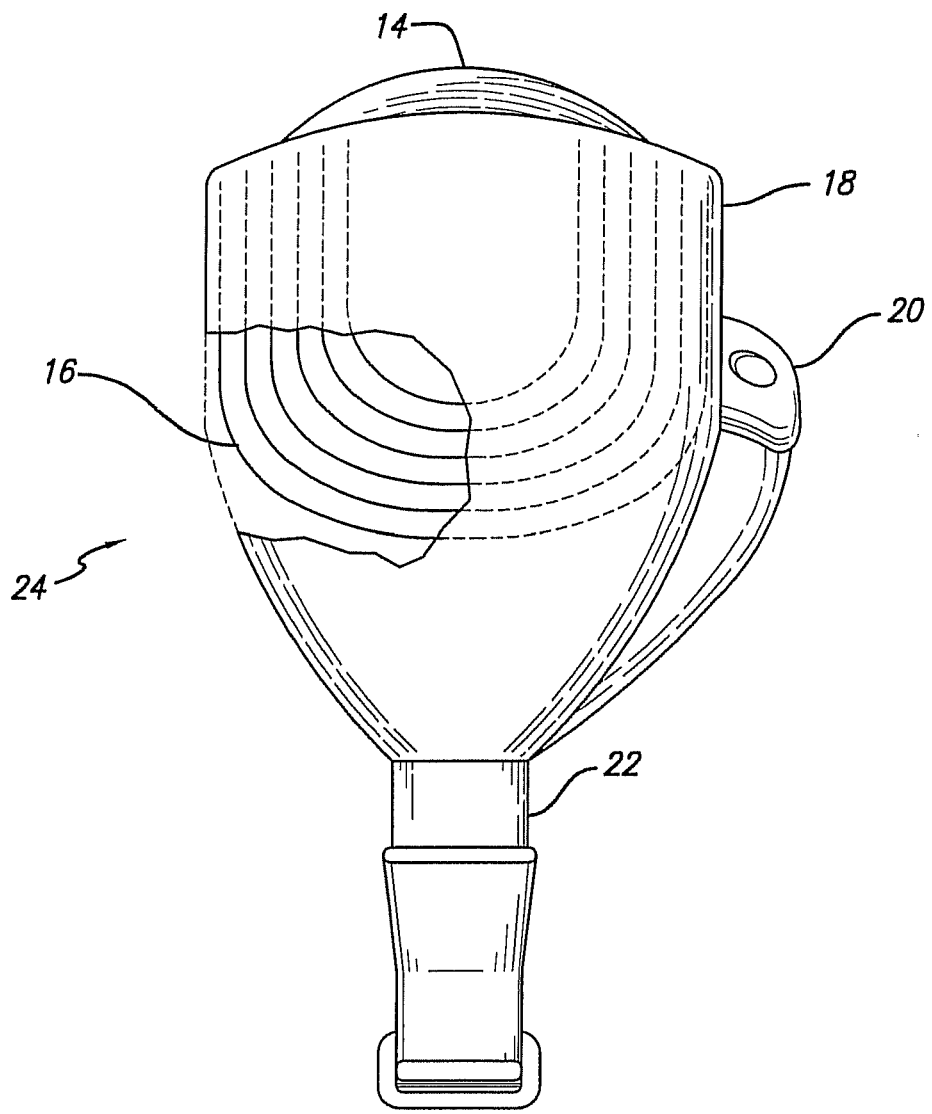
FIG. 2 is a side view of the implanted portion of the preferred retinal prosthesis showing the fan tail in more detail.
Figure 3A:
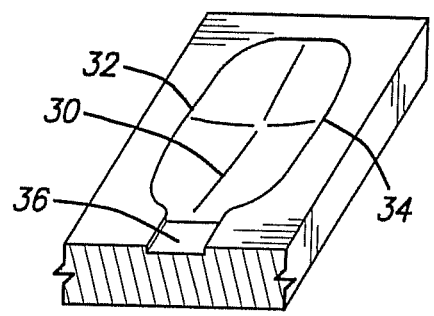
FIG. 3A-3E depict molds for forming the flexible circuit array in a curve.
Figure 3B:
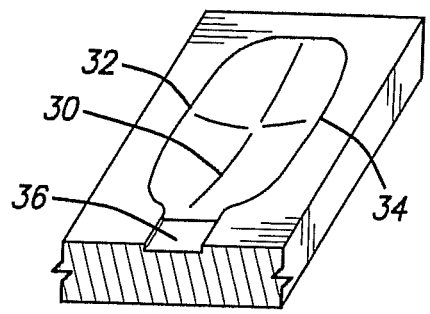
Figure 3C:
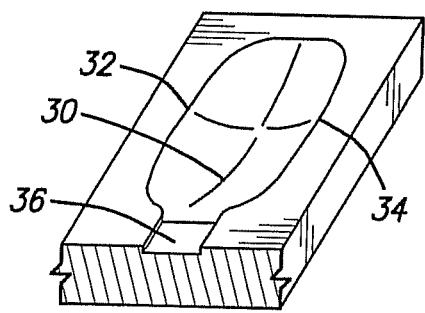
Figure 3D:
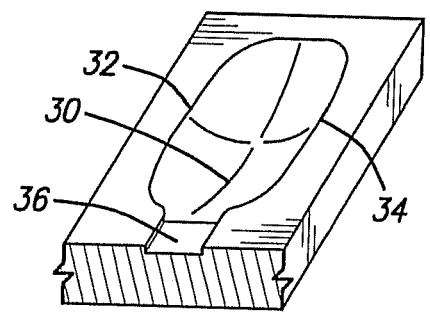
Figure 3E:
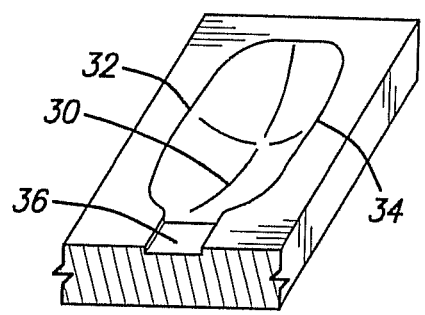

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrode and bond pad to improve electrical continuity. This can be accomplished through any of the above methods or electroplating. Then, the top layer of polymer is applied over the metal. Openings in the top layer for electrical contact to the electronics package 14 and the electrodes may be accomplished by laser ablation or reactive ion etching (RIE) or photolithography and wet etch. Making the electrode openings in the top layer smaller than the electrodes promotes adhesion by avoiding delamination around the electrode edges.

The pressure applied against the retina by the flexible circuit electrode array 10 is critical. Too little pressure causes increased electrical resistance between the array 10 and retina. It should be noted that while the present invention is described in terms of application to the retina, the techniques described are equally applicable to many forms of neural stimulation. Application to the retina requires a convex spherical curve. Application to the cochlea requires a constant curve in one dimension and a spiral curve in the other. Application to the cerebral cortex requires a concave spherical curve. Cortical stimulation is useful for artificial vision or hearing, touch and motor control for limb prostheses, deep brain stimulation for Parkinson's disease and multiple sclerosis, and many other applications.

Common flexible circuit fabrication techniques such as photolithography generally require that a flexible circuit electrode array 10 be made flat. Since the retina is spherical, a flat array 10 will necessarily apply more pressure near its edges, than at its center. With most polymers, it is possible to curve them when heated in a mold. By applying the right amount of heat to a completed array 10, a curve can be induced that matches the curve of the retina. To minimize warping, it is often advantageous to repeatedly heat the flexible circuit in multiple molds, each with a decreasing radius. FIG. 3 illustrates a series of molds according to the preferred embodiment. Since the flexible circuit will maintain a constant length, the curvature must be slowly increased along that length. As the curvature 30 decreases in successive molds (FIGS. 3A-3E) the straight line length between ends 32 and 34, must decrease to keep the length along the curvature 30 constant, where mold 3E approximates the curvature of the retina or other desired neural tissue. The molds provide a further opening 36 for the flexible circuit cable 12 of the array 10 to exit the mold without excessive curvature.

It should be noted that suitable polymers include thermoplastic materials and thermoset materials. While a thermoplastic material will provide some stretch when heated a thermoset material will not. The successive molds are, therefore, advantageous only with a thermoplastic material. A thermoset material works as well in a single mold as it will with successive smaller molds. It should be noted that, particularly with a thermoset material, excessive curvature in three dimensions will cause the polymer material to wrinkle at the edges. This can cause damage to both the array 10 and the retina. Hence, the amount of curvature is a compromise between the desired curvature, array surface area, and the properties of the material.

Figure 4:
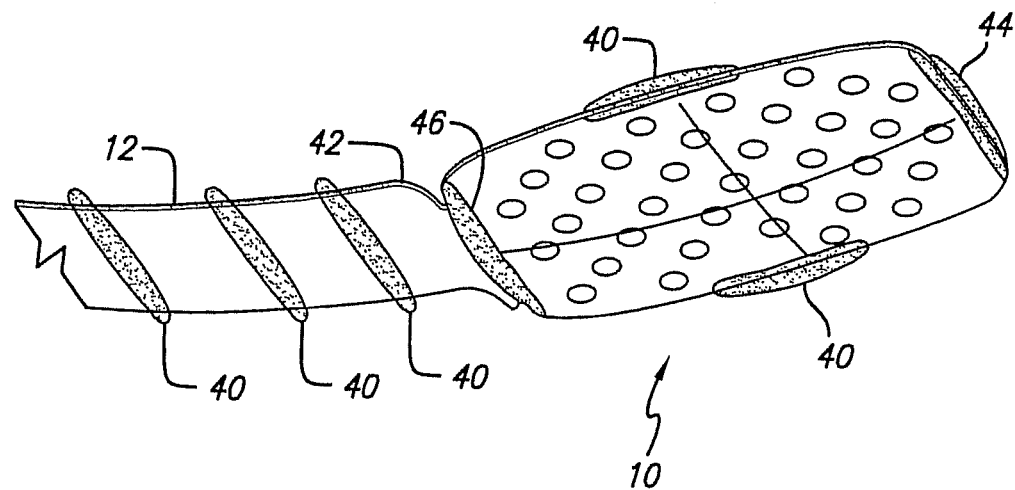
FIG. 4 depicts an alternate view of the invention with ribs to help maintain curvature and prevent retinal damage.

Referring to FIG. 4, the edges of the polymer layers are often sharp. There is a risk that the sharp edges of a flexible circuit will cut into delicate retinal tissue. It is advantageous to add a soft material, such as silicone, to the edges of a flexible circuit electrode array 10 to round the edges and protect the retina. Silicone around the entire edge is preferable, but may make the flexible circuit less flexible. So, another embodiment as depicted in FIG. 4 has discrete silicone bumpers or ribs to hold the edge of the flexible circuit electrode array 10 away from the retinal tissue. Curvature 40 fits against the retina. The leading edge 44 is most likely to cause damage and is therefore fit with molded silicone bumper. Also, edge 46, where the array 10 lifts off the retina can cause damage and should be fit with a bumper. Any space along the side edges of curvature 40 may cause damage and may be fit with bumpers as well. It is also possible for the flexible circuit cable 12 of the electrode array 10 to contact the retina. It is, therefore, advantageous to add periodic bumpers along the flexible circuit cable 12.

It is also advantageous to create a reverse curve or service loop in the flexible circuit cable 12 of the flexible circuit electrode array 10 to gently lift the flexible circuit cable 12 off the retina and curve it away from the retina, before it passes through the sclera at a sclerotomy. It is not necessary to heat curve the service loop as described above, the flexible circuit electrode array 10 can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array 10 must pass through the sclera to in order be inside the eye and contact the retina. The sclera is cut through at the pars plana, forming a sclerotomy, and the flexible circuit passed through the sclerotomy. A flexible circuit is thin but wide. The more electrode conductors, the wider the flexible circuit must be. It may be difficult to seal a sclerotomy over a flexible circuit wide enough to support enough conductors for a high resolution array 10 unless multiple conductor layers are employed. A narrow sclerotomy is preferable.

Figure 5:
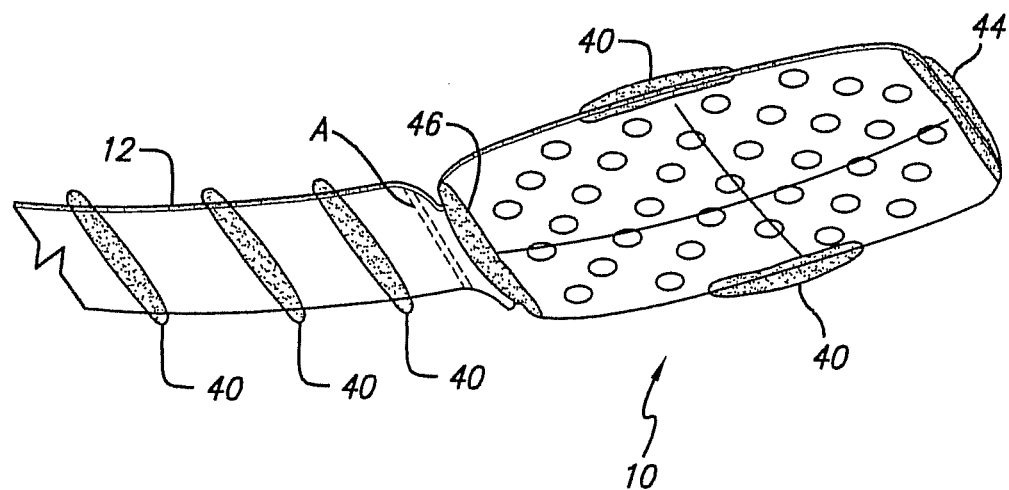
FIG. 5 depicts an alternate view of the invention with ribs to help maintain curvature and prevent retinal damage fold of the flexible circuit cable and a fold A between the circuit electrode array and the flexible circuit cable.

FIG. 5 depicts a further embodiment of the part of the prosthesis shown in FIG. 4 with a fold A between the flexible circuit electrode array 10 and the flexible circuit cable 12. The angle in the fold A also called ankle has an angle of 1°-180°, preferably 80°-120°. The fold A is advantageous since it reduces tension and enables an effective attachment of the flexible electrode circuit array 10 to the retina.

Figure 6:
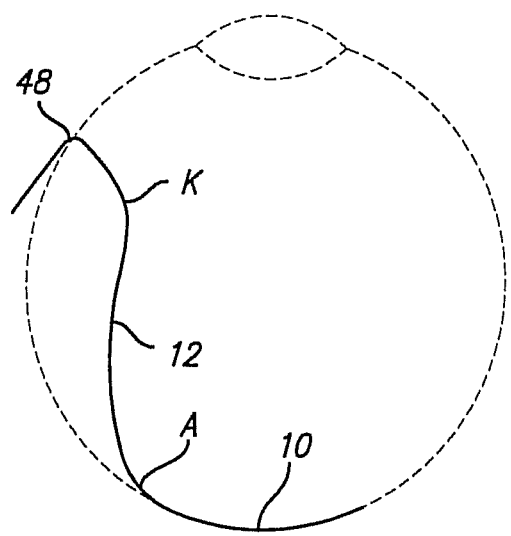
FIG. 6 depicts a cross-sectional view of the prosthesis shown insight of the eye with an angle in the fold of the flexible circuit cable and a fold between the circuit electrode array and the flexible circuit cable.

FIG. 6 depicts a side view of the prosthesis insight of the eye with an angle K of the flexible circuit cable 12 and a fold A between the circuit electrode array 10 and the flexible circuit cable 12. Fold K may alternatively be located at the sclerotomy. The angle K is about 45°-180° and preferably 80°-100°. The fold K also called knee is advantageous because it decreases force which would be applied by the flexible circuit cable 12 on the electrode region 10. Since the magnitude and direction of this force varies greatly with eye size it is best to minimize the effect of this force on the important electrode region of the flexible circuit electrode array 10 in order to maintain equal performance across a range of eye sizes. Additionally the fold K keeps the flexible circuit cable 12 from blocking the surgeon's view of the electrode region 10 during surgery. Visualization of the electrode region 10 during surgery is very important during the attachment of the flexible circuit electrode array 10 to the retina in order to permit correct positioning.

Figure 7:
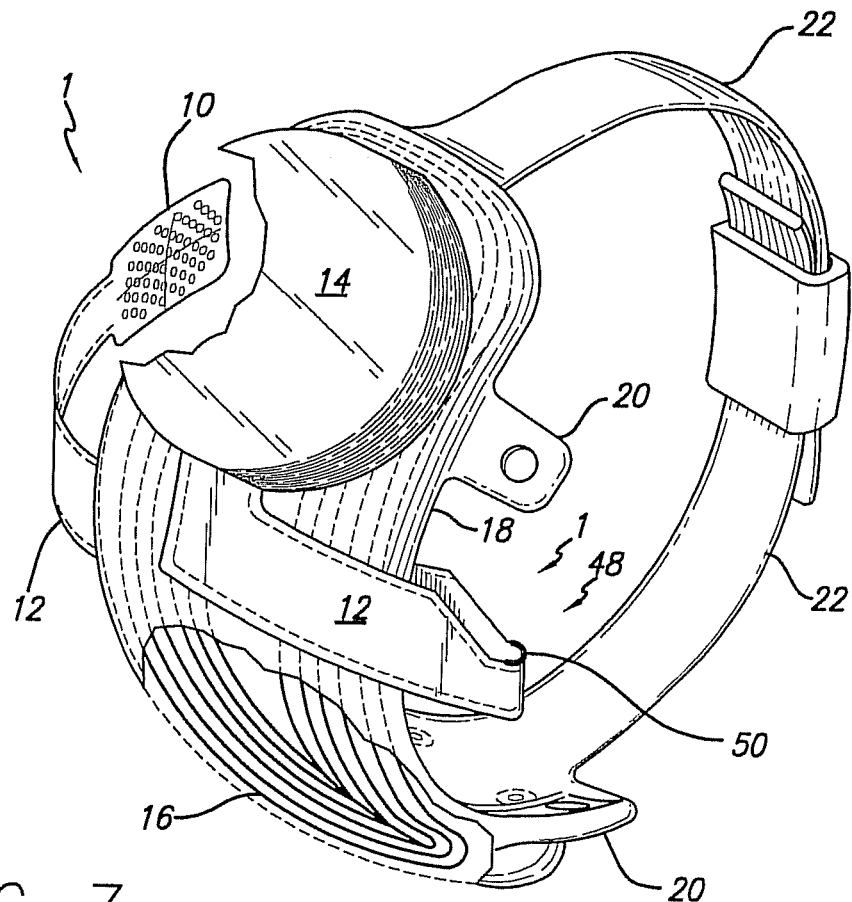
FIG. 7 depicts the implanted portion including a twist in the array to reduce the width of a sclerotomy and a sleeve to promote sealing of the sclerotomy.

FIG. 7 shows the implanted portion of the retinal prosthesis including the additional feature of a twist or fold 48 in the flexible circuit cable 12, where the flexible circuit cable 12 passes through the sclera (sclerotomy). The twist may be a simple sharp twist, or fold 48; or it may be a longer twist, forming a tube. While the tube is rounder, it reduces the flexibility of the flexible circuit. A simple fold 48 reduces the width of the flexible circuit with only minimal impact on flexibility.

Further, silicone or other pliable substance may be used to fill the center of the tube or fold 48 formed by the twisted flexible circuit cable 12. Further it is advantageous to provide a sleeve or coating 50 that promotes sealing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-tex or similar material would bond with scleral tissue and promote healing. In particular, a porous material will allow scleral tissue to grow into the pores promoting a good bond.

Alternatively, the flexible circuit electrode array 10 may be inserted through the sclera, behind the retina and placed between the retina and choroid to stimulate the retina subretinally. In this case, it is advantageous to provide a widened portion, or stop, of the flexible circuit cable 12 to limit how far the flexible circuit electrode array 10 is inserted and to limit the transmission of stress through the sclera. The stop may be widening of the flexible circuit 1 or it may be added material such as a bumper or sleeve.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 10 that is wider than it is tall. This is equally applicable to a cortical visual array 10. In which case, the wider dimension is not horizontal on the visual cortex, but corresponds to horizontal in the visual scene.

Figure 8:
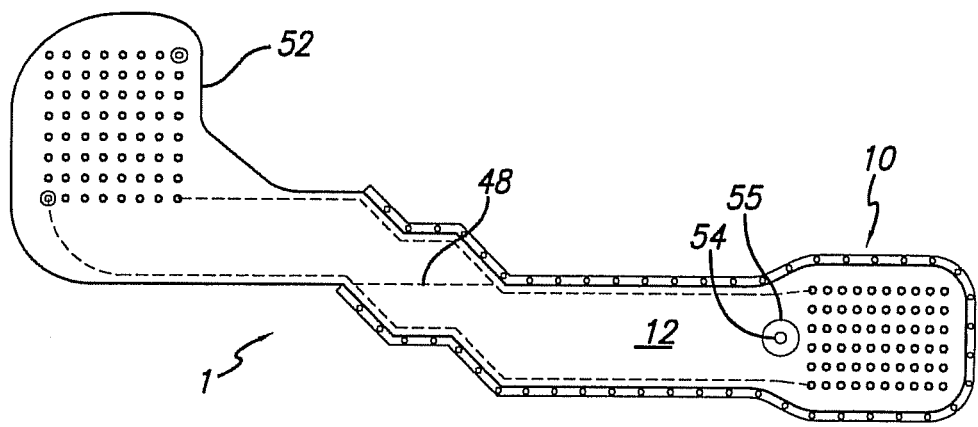
FIG. 8 depicts the flexible circuit array before it is folded and attached to the implanted portion.

FIG. 8 shows the flexible circuit electrode array 10 prior to folding and attaching the array 10 to the electronics package. At one end of the flexible circuit cable 12 is an interconnection pad 52 for connection to the electronics package. At the other end of the flexible circuit cable 12 is the flexible circuit electrode array 10. Further, an attachment point 54 is provided near the flexible circuit electrode array 10. A retinal tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

Figure 9:
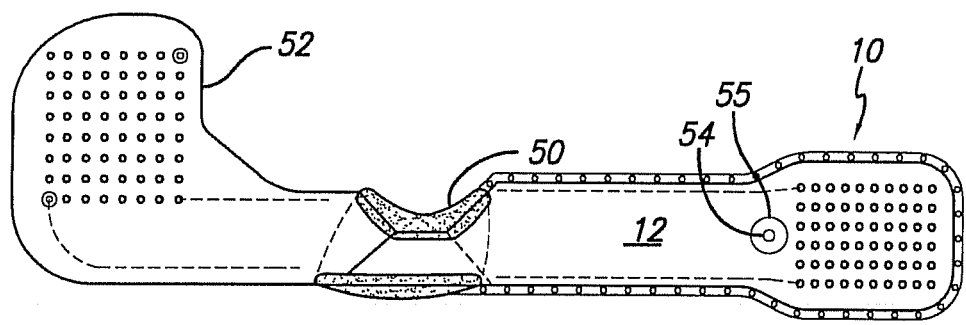
FIG. 9 depicts the flexible circuit array folded.

FIG. 9 shows the flexible circuit electrode array 10 after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture.

An alternative to the bumpers described in FIG. 4, is a skirt of silicone or other pliable material as shown in FIGS. 11, 12, 13 and 14. A skirt 60 covers the flexible circuit electrode array 10, and extends beyond its edges. It is further advantageous to include wings 62 adjacent to the attachment point 54 to spread any stress of attachment over a larger area of the retina. There are several ways of forming and bonding the skirt 60. The skirt 60 may be directly bonded through surface activation or indirectly bonded using an adhesive.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such a polyimide may be used for the bottom layer and a relatively softer polymer such a silicone may be used for the top layer including an integral skirt to protect delicate neural tissue. The said top layer is the layer closest to the retina.

Figure 11:
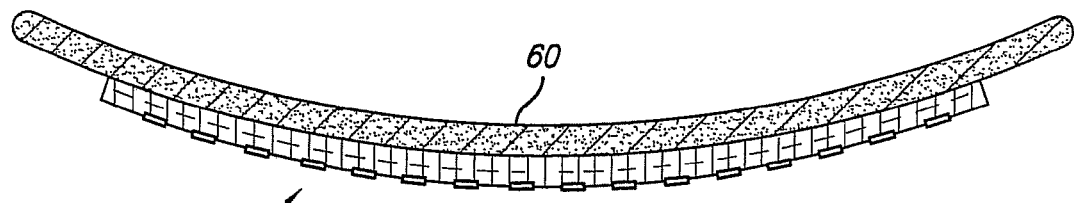
FIG. 11 depicts a flexible circuit array with a protective skirt bonded to the back side of the flexible circuit array.
Figure 12:
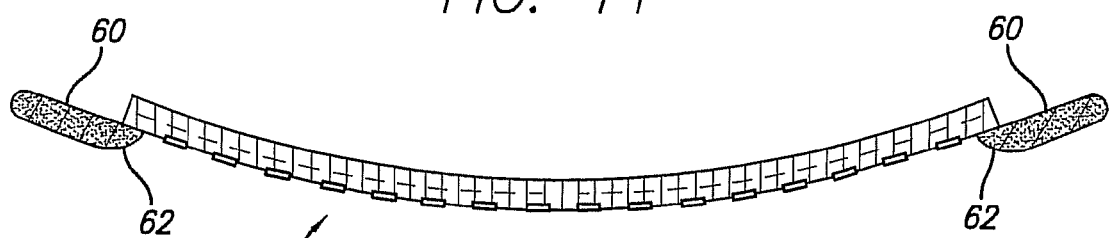
FIG. 12 depicts a flexible circuit array with a protective skirt bonded to the front side of the flexible circuit array.

The simplest solution is to bond the skirt 60 to the back side (away from the retina) of the flexible circuit electrode array 10 as shown in FIG. 11. While this is the simplest mechanical solution, sharp edges of the flexible circuit electrode array 10 may contact the delicate retina tissue. Bonding the skirt to the front side (toward the retina) of the flexible circuit electrode array 10, as shown in FIG. 12, will protect the retina from sharp edges of the flexible circuit electrode array 10. However, a window 62 must be cut in the skirt 60 around the electrodes. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

Figure 13:
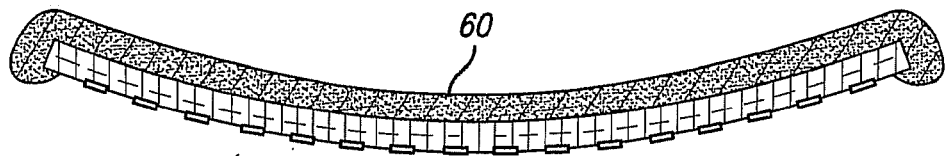
FIG. 13 depicts a flexible circuit array with a protective skirt bonded to the back side of the flexible circuit array and molded around the edges of the flexible circuit array.

FIG. 13 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side, of the flexible circuit electrode array 10, the portion extending beyond the front side of the flexible circuit electrode array 10 can be much smaller. This limits any additional spacing between the electrodes and the retinal tissue.

Figure 14:
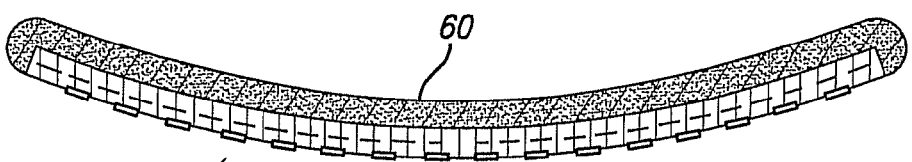
FIG. 14 depicts a flexible circuit array with a protective skirt bonded to the back side of the flexible circuit array and molded around the edges of the flexible circuit array and flush with the front side of the array.

FIG. 14 shows a flexible circuit electrode array 10 similar to FIG. 13, with the skirt 60, flush with the front side of the flexible circuit electrode array 10 rather than extending beyond the front side. While this is more difficult to manufacture, it does not lift the electrodes off the retinal surface as with the array 10 in FIG. 10. It should be noted that FIGS. 11, 13, and 14 show skirt 60 material along the back of the flexible circuit electrode array 10 that is not necessary other than for bonding purposes. If there is sufficient bond with the flexible circuit electrode array 10, it may advantageous to thin or remove portions of the skirt 60 material for weight reduction.

Figure 10:
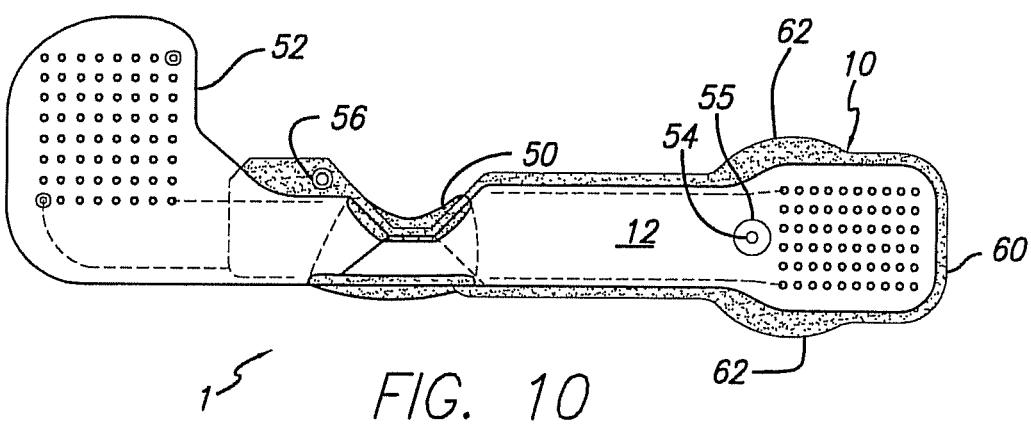
FIG. 10 depicts a flexible circuit array with a protective skirt.
Figure 15:
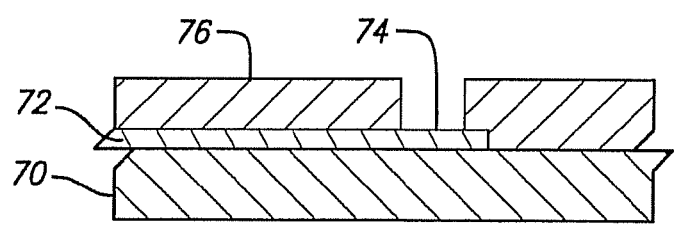
FIG. 15 is an enlarged view of a single electrode within the flexible circuit electrode array.

Referring to FIG. 15, the flexible circuit electrode array 10 is manufactured in layers. A base layer of polymer 70 is laid down, commonly by some form of chemical vapor deposition, spinning, meniscus coating or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIGS. 8-10). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Figure 16:
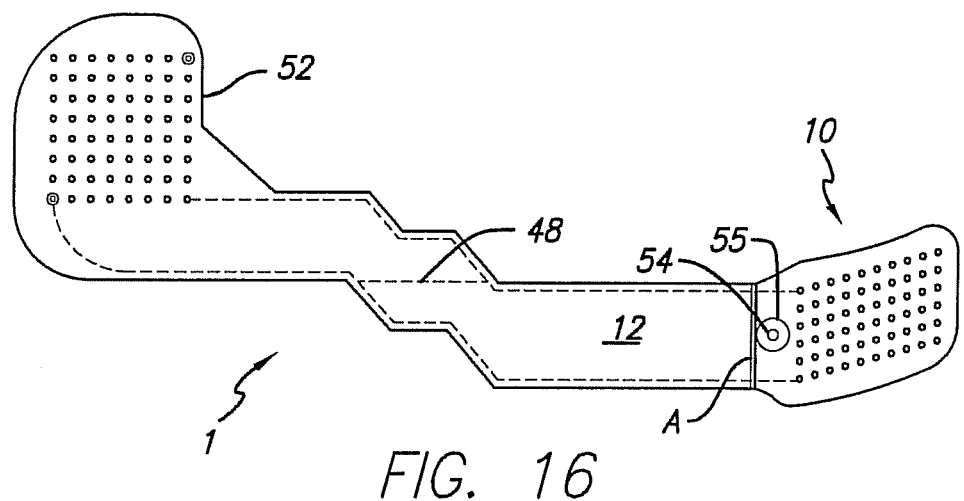
FIG. 16 depicts the flexible circuit array before it is folded and attached to the implanted portion containing an additional fold between the flexible electrode array and the flexible cable.

FIG. 16 depicts the flexible circuit array 10 before it is folded and attached to the implanted portion containing an additional fold A between the flexible electrode array 10 and the flexible cable 12. The angle in the fold A also called ankle has an angle of 1°-180°, preferably 80°-120°. The ankle is advantageous in the process of inserting the prostheses in the eye and attaching it to the retina.

Figure 17:
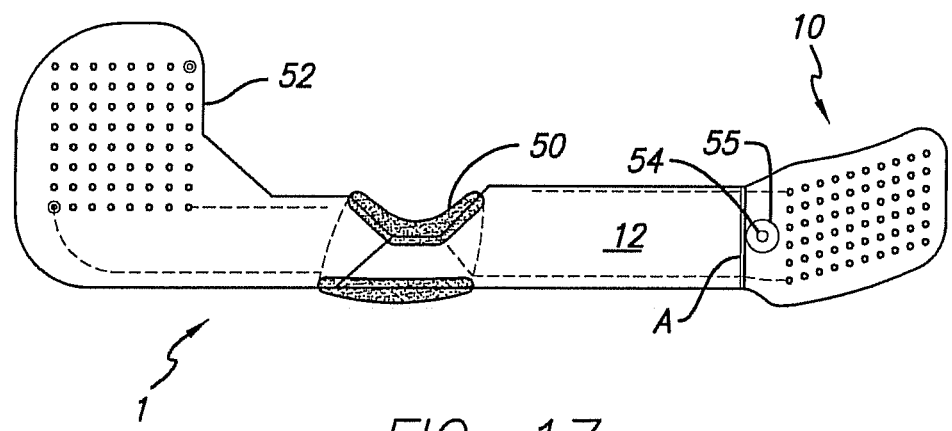
FIG. 17 depicts the flexible circuit array of FIG. 16 folded containing an additional fold between the flexible electrode array and the flexible cable.

FIG. 17 depicts the flexible circuit array 10 containing an additional fold A between the flexible electrode array 10 and the flexible cable 12. The flexible circuit array 10 as shown in FIGS. 8 and 16 differ by the fold A from each other.

Figure 18:
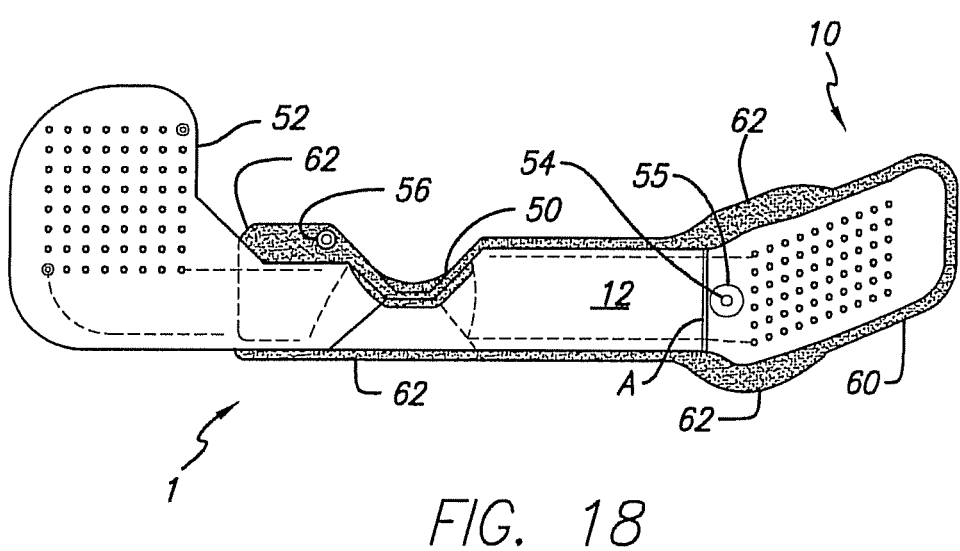
FIG. 18 depicts a flexible circuit array of FIG. 17 with a protective skirt and containing an additional fold between the flexible electrode array and the flexible cable.

FIG. 18 depicts a flexible circuit array 10 of FIG. 17 with a protective skirt 60 and containing an additional fold A between the flexible electrode array 10 and the flexible cable 12. The flexible circuit array 10 as shown in FIGS. 10 and 18 differ by the fold A from each other.

Figure 21:
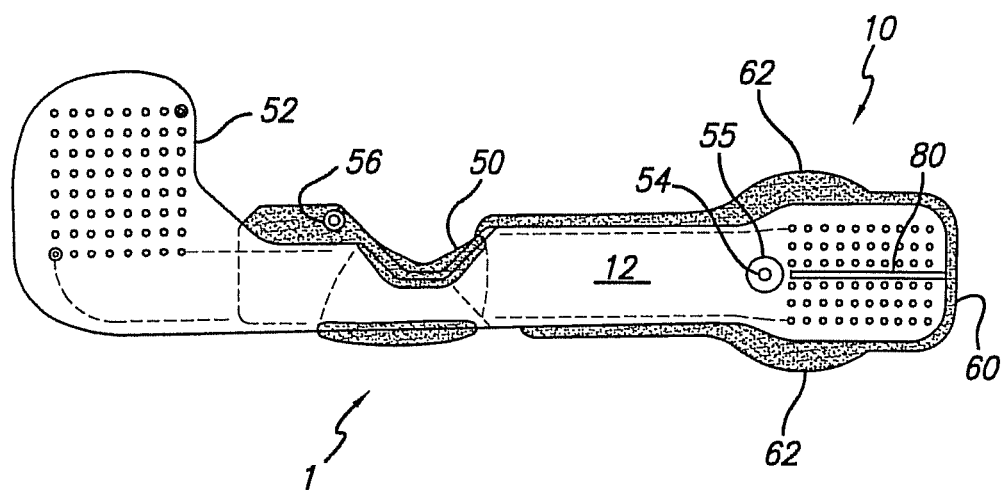
FIG. 21 depicts a top view of a flexible circuit array and flexible circuit cable wherein the array contains a slit along the length axis.

FIG. 21 depicts a top view of a flexible circuit array 10 and flexible circuit cable 12 as shown in FIGS. 10, 18, 19, and 20 wherein the array 10 in FIG. 21 contains a slit along the length axis.

Figure 22:
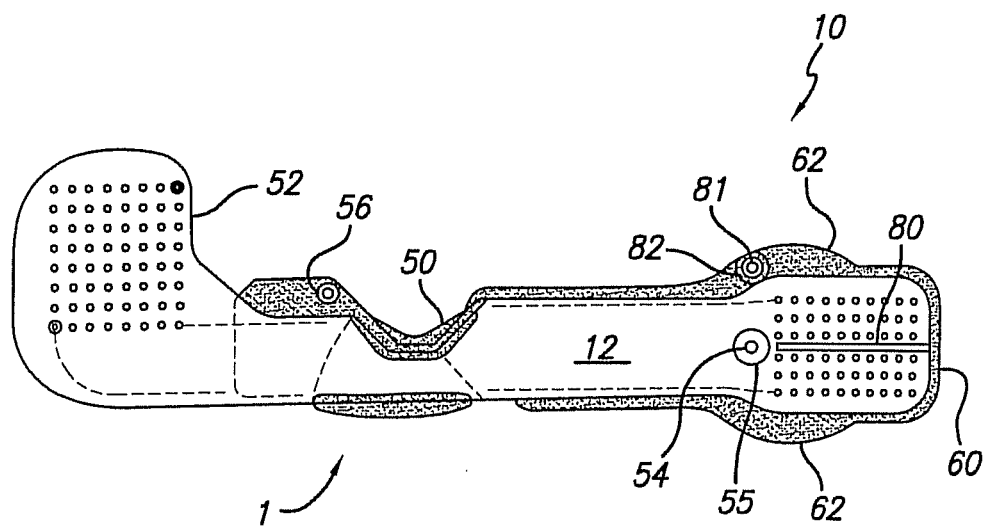
FIG. 22 depicts a top view of a flexible circuit array and flexible circuit cable wherein the array contains a slit along the length axis with a two attachment points.

FIG. 22 depicts a skirt of silicone or other pliable material as shown in FIGS. 10 to 14. A skirt 60 covers the flexible circuit electrode array 10, and extends beyond its edges. In this embodiment of the present invention the flexible circuit electrode array 10 contains a slit 80 along the lengths axis. Further, according to this embodiment the skirt of silicone or other pliable material contains preferably at least two attachment points 81 and stress relieves 82 are provided surrounding the attachment points 81. The attachment points 81 are located preferably on the skirt 60 outside the flexible circuit electrode 10 and are positioned apart as far as possible from each other. The secondary tack 81 is far enough away from the first tack location 54 not to cause tenting, therefore fibrosis between the two tacks which cause a traction detachment of the retina. Furthermore, the polyimide is completely between the two tacks, which also reduce the possibility of tenting. Also, this orientation of tacks keeps the tacks away from the axons, which arise from the ganglion cells which are tried to be activated. They are away from the raffe. The wings act like external tabs or strain relieves. The multiple tacks prevent rotation of the array 10. Alternatively the secondary tack could be placed at an attachment point at 83.

The stress relief 82 may be made of a softer polymer than the flexible circuit, or it may include cutouts or thinning of the polymer to reduce the stress transmitted from the retina tack to the flexible circuit electrode array 10.

Figure 23:
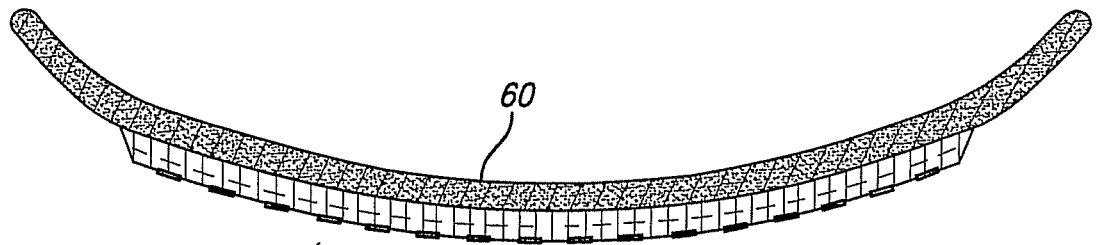
FIG. 23 depicts a flexible circuit array with a protective skirt bonded to the back side of the flexible circuit array with a progressively decreasing radius.

FIG. 23 depicts a flexible circuit array 10 with a protective skirt 60 bonded to the back side of the flexible circuit array 10 with a progressively decreasing radius and/or decreasing thickness toward the edges.

Figure 24:
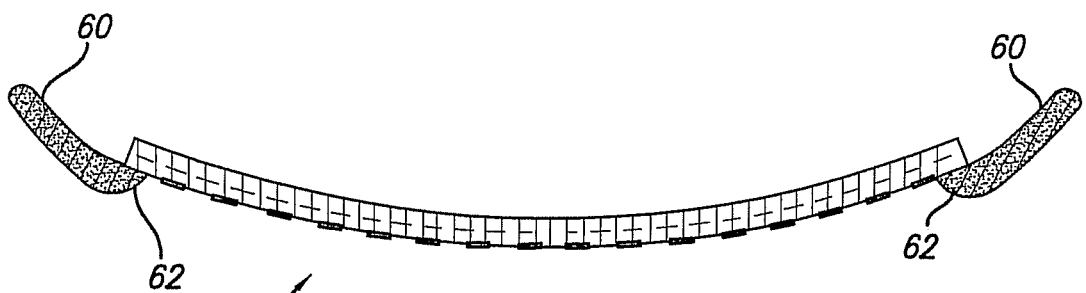
FIG. 24 depicts a flexible circuit array with a protective skirt bonded to the front side of the flexible circuit array with a progressively decreasing radius.

FIG. 24 depicts a flexible circuit array 10 with a protective skirt 60 bonded to the front side of the flexible circuit array 10 with a progressively decreasing radius and/or decreasing thickness toward the edges.

Figure 25:
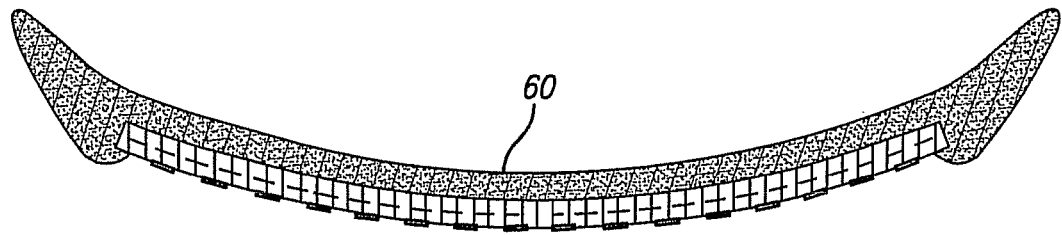
FIG. 25 depicts a flexible circuit array with a protective skirt bonded to the back side of the flexible circuit array and molded around the edges of the flexible circuit array with a progressively decreasing radius.

FIG. 25 depicts a flexible circuit array 10 with a protective skirt 60 bonded to the back side of the flexible circuit array 10 and molded around the edges of the flexible circuit array 10 with a progressively decreasing radius and/or decreasing thickness toward the edges.

Figure 26:
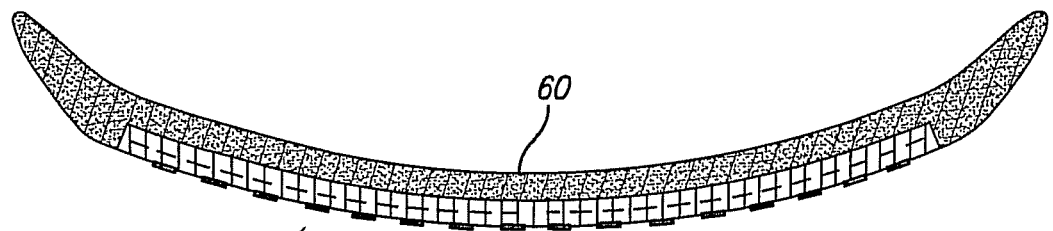
FIG. 26 depicts a flexible circuit array with a protective skirt bonded to the back side of the flexible circuit array and molded around the edges of the flexible circuit array and flush with the front side of the array with a progressively decreasing radius.

FIG. 26 depicts a flexible circuit array 10 with a protective skirt 60 bonded to the back side of the flexible circuit array 10 and molded around the edges of the flexible circuit array 10 and flush with the front side of the array 10 with a progressively decreasing radius and/or decreasing thickness toward the edges.

Figure 27:
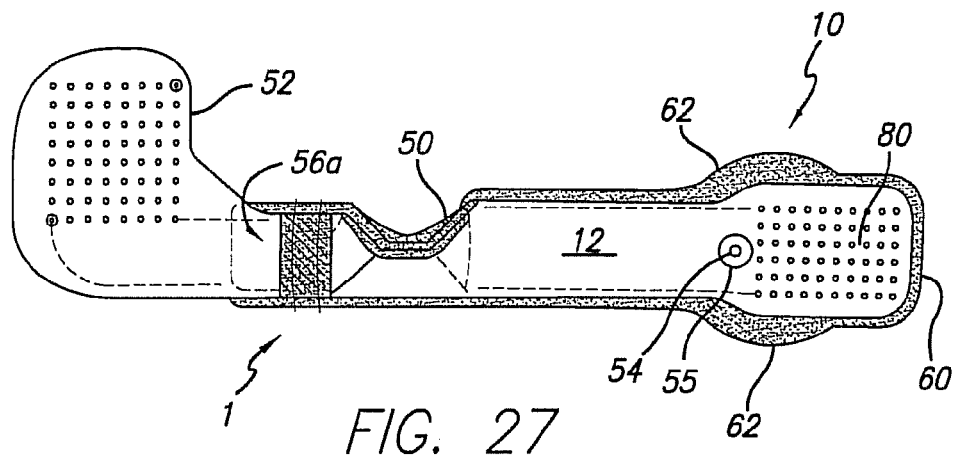
FIG. 27 depicts a side view of the flexible circuit array with a skirt containing a grooved and rippled pad instead a suture tab.
Figure 28:
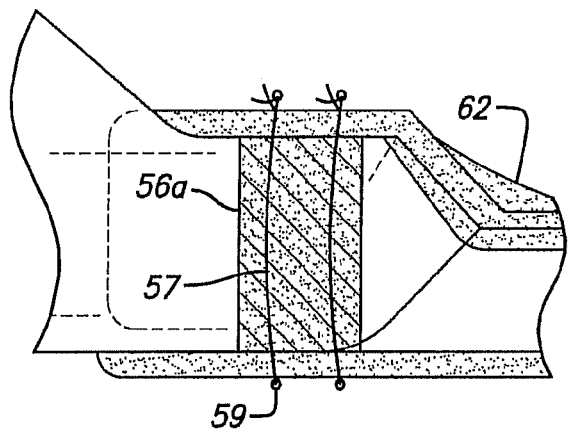
FIG. 28 depicts a side view of the enlarged portion of the skirt shown in FIG. 27 containing a grooved and rippled pad and a mattress suture.

FIG. 27 depicts a side view of the array 10 with a skirt 60 containing a grooved and rippled pad 56a instead a suture tab 56. This pad 56a has the advantage of capturing a mattress suture 57. A mattress suture 57 has the advantage of holding the groove or rippled pad 56a in two places as shown in FIG. 28. Each suture 57 is fixed on the tissue on two places 59. A mattress suture 57 on a grooved or rippled mattress 56a therefore provides a better stability.

Figure 29:
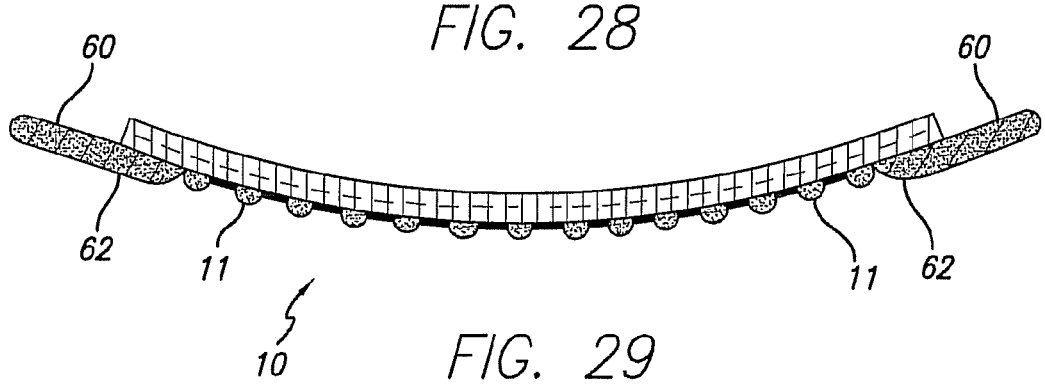
FIG. 29 depicts a flexible circuit array with a protective skirt bonded to the front side of the flexible circuit array with individual electrode windows.

FIG. 29 depicts a flexible circuit array 10 with a protective skirt 60 bonded to the front side of the flexible circuit array 10 with individual electrode 13 windows and with material, preferably silicone between the electrodes 13.

Figure 30:
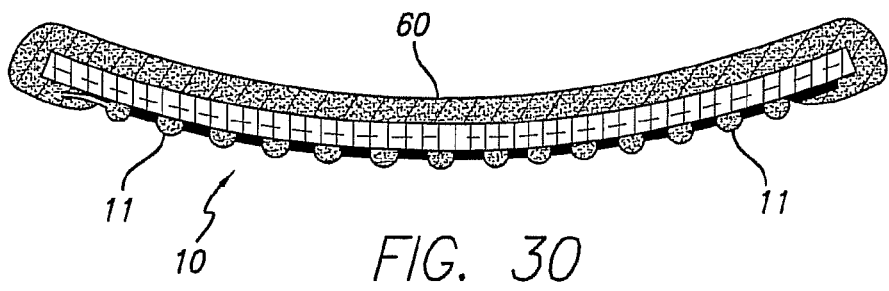
FIG. 30 depicts a flexible circuit array with a protective skirt bonded to the back side of the flexible circuit array and molded around the edges of the flexible circuit array with individual electrode windows.

FIG. 30 depicts a flexible circuit array 10 with a protective skirt bonded to the back side of the flexible circuit array 10 and molded around the edges of the flexible circuit array 10 with individual electrode windows and with material, preferably silicone between the electrodes 13.

FIGS. 31-36 show several surfaces to be applied to one or both sides of the flexible circuit array cable 12. The surfaces are thin films containing a soft polymer, preferably silicone. FIG. 31 shows a flange 15: A flange 15 can be a solid film of material containing silicone added to the surface of the polymer containing polyimide. FIGS. 32-34 show a ladder 15a: A ladder 15a is a flange with material removed from central portions in some shape 19. FIG. 35 shows a skeleton structure 15*b*. A skeleton 15*b* is a flange with material removed from perimeter portions in some shape 21. FIG. 36 shows a structure 15*c* with beads 23 and bumpers 25. A bead 23 is material added to perimeter portions of the polymer cable 12 in some shape without material being added on the central area. A bumper 25 can be an extended or continuous version of the beaded approach. Both approaches are helpful in preventing any possible injury of the tissue by the polymer.

Figure 37:
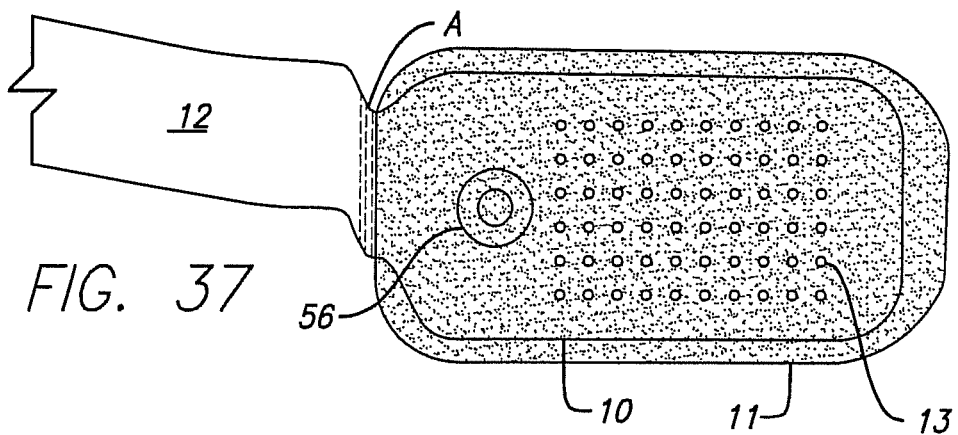
FIG. 37 depicts the top view of the flexible circuit array being enveloped within an insulating material.

FIG. 37 depicts the top view of the flexible circuit array 10 being enveloped within an insulating material 11. The electrode array 10 comprises oval-shaped electrode array body 10, a plurality of electrodes 13 made of a conductive material, such as platinum or one of its alloys, but that can be made of any conductive biocompatible material such as iridium, iridium oxide or titanium nitride. The electrode array 10 is enveloped within an insulating material 11 that is preferably silicone. "Oval-shaped" electrode array 10 body means that the body may approximate either a square or a rectangle shape, but where the corners are rounded. This shape of an electrode array 10 is described in the U.S. Patent Application No. 20020111658, entitled "Implantable retinal electrode array 10 configuration for minimal retinal damage and method of reducing retinal stress" and No. 20020188282, entitled "Implantable drug delivery device" to Robert J. Greenberg et al., the disclosures of both are incorporated herein by reference.

The material body 11 is made of a soft material that is compatible with the electrode array body 10. In a preferred embodiment the body 11 made of silicone having hardness of about 50 or less on the Shore A scale as measured with a durometer. In an alternate embodiment the hardness is about 25 or less on the Shore A scale as measured with a durometer.

Figure 38:
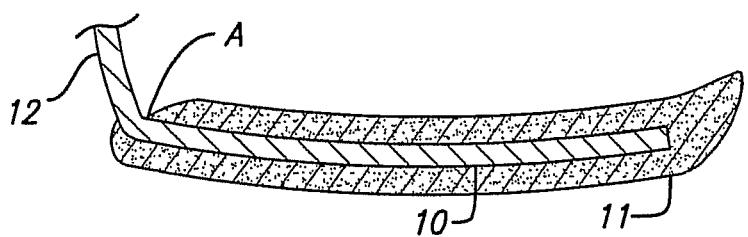
FIG. 38 depicts a cross-sectional view of the flexible circuit array being enveloped within an insulating material.

FIG. 38 depicts a cross-sectional view of the flexible circuit array 10 being enveloped within an insulating material 11. It shows how the edges of the material body 11 are lifted off due to the contracted radius at the edges. The electrode array 10 preferably also contains a fold A between the cable 12 and the electrode array 10. The angle of the fold A secures a relief of the implanted material.

Figure 39:
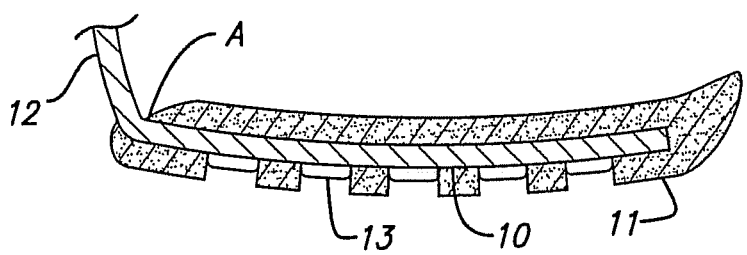
FIG. 39 depicts a cross-sectional view of the flexible circuit array being enveloped within an insulating material with open electrodes and the material between the electrodes.

FIG. 39 depicts a cross-sectional view of the flexible circuit array 10 being enveloped within an insulating material 11 with open electrodes 13 and the material 11 between the electrodes 13.

Figure 40:
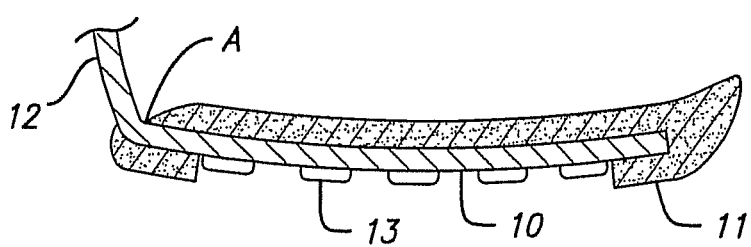
FIG. 40 depicts a cross-sectional view of the flexible circuit array being enveloped within an insulating material with open electrodes.

FIG. 40 depicts a cross-sectional view of the flexible circuit array 10 being enveloped within an insulating material 11 with open electrodes 13. This is another embodiment wherein the electrodes 13 are not separated by the material 11 but the material 11 is extended.

Figure 41:
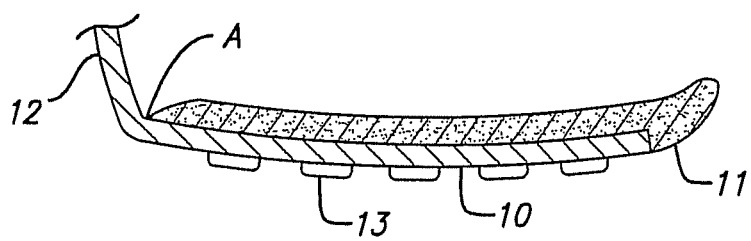
FIG. 41 depicts a cross-sectional view of the flexible circuit array being enveloped within an insulating material with electrodes on the surface of the material.

FIG. 41 depicts a cross-sectional view of the flexible circuit array 10 being enveloped within an insulating material 11 with electrodes 13 on the surface of the material 11. This is a further embodiment with the electrode 13 on the surface of the material 11, preferably silicone. The embodiments shown in FIGS. 39, 40, and 41 show a preferred body 11 containing silicone with the edges being lifted off from the retina due to contracted radius of the silicone body 11 at the edges.

Figure 42:
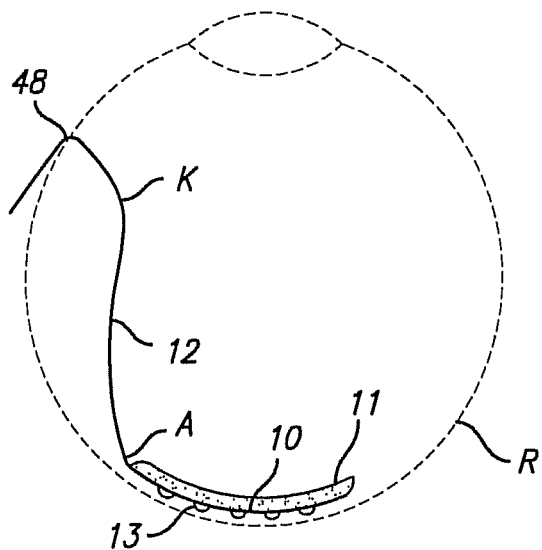
FIG. 42 depicts a cross-sectional view of the flexible circuit array being enveloped within an insulating material with electrodes on the surface of the material insight the eye with an angle in the fold of the flexible circuit cable and a fold between the circuit electrode array and the flexible circuit cable.

FIG. 42 depicts a cross-sectional view of the flexible circuit array 10 being enveloped within an insulating material 11 with electrodes 13 on the surface of the material 11 insight the eye with an angle K in the fold of the flexible circuit cable 12 and a fold A between the circuit electrode array 10 and the flexible circuit cable 12. The material 11 and electrode array body 10 are in intimate contact with retina R. The surface of electrode array body 10 in contact with retina R is a curved surface with a matched radius compared to the spherical curvature of retina R to minimize pressure concentrations therein. Further, the decreasing radius of spherical curvature of material 11 near its edge forms edge relief that causes the edges of the body 11 to lift off the surface of retina R eliminating pressure concentrations at the edges. The edge of body 11 is rounded to reduce pressure and cutting of retina R.

Figure 43:
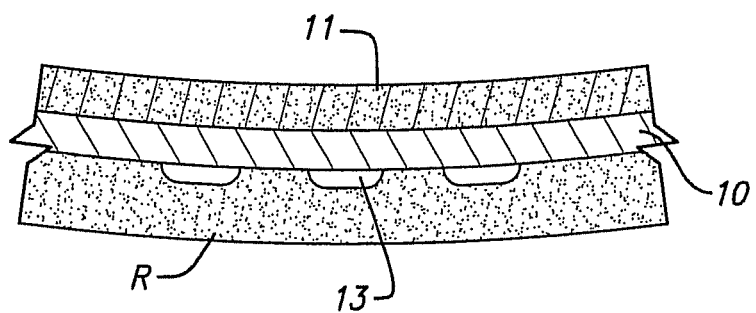
FIG. 43 depicts a side view of the enlarged portion of the flexible circuit array being enveloped within an insulating material with electrodes on the surface of the material insight the eye.

FIG. 43 shows a part of the FIG. 42 enlarged showing the electrode array 10 and the electrodes 13 enveloped by the polymer material, preferably silicone 11 in intimate contact with the retina R.

The electrode array 10 embedded in or enveloped by the polymer material, preferably silicone 11 can be preferably produced through the following steps. The soft polymer material which contains silicone is molded into the designed shape and partially hardened. The electrode array 10 which preferably contains polyimide is introduced and positioned in the partially hardened soft polymer containing silicone. Finally, the soft polymer 11 containing silicone is fully hardened in the designed shape enveloping the electrode array 10. The polymer body 11 has a shape with a decreasing radius at the edges so that the edges of the body 11 lift off from the retina R.

Figure 44:
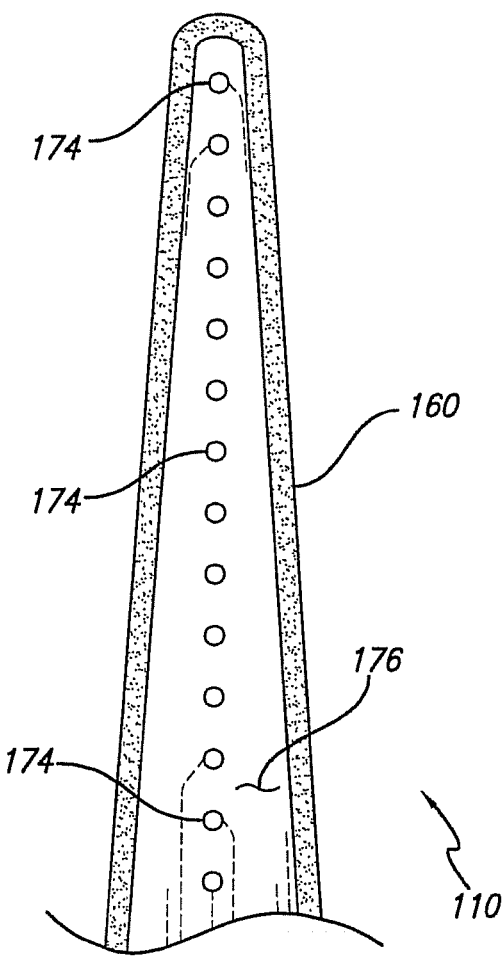
FIG. 44 shows of front view of a cochlear electrode array according to the present invention.
Figure 45:
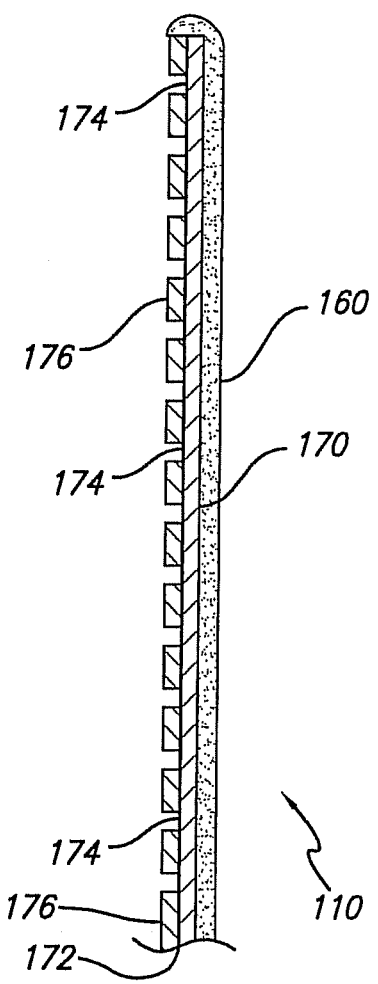
FIG. 45 shows a side view of a cochlear electrode array according to the present invention.
Figure 46:
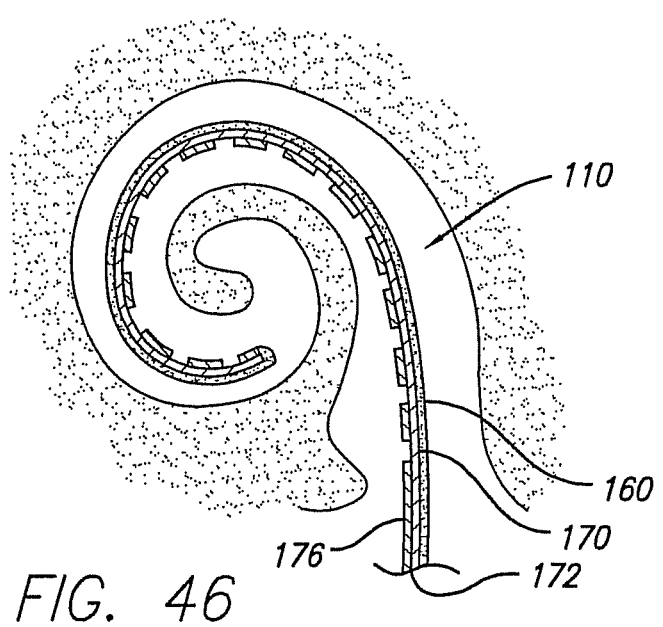
FIG. 46 shows a cochlear electrode array according to the present invention as implanted in the cochlea.

FIGS. 44-46 show application of the present invention to a cochlear prosthesis. FIG. 44 shows of front view of cochlear electrode array 110. The cochlear electrode array 110 tapers toward the top to fit in an ever smaller cochlea and because less width is required toward the top for metal traces. The electrodes 174 are arranged linearly along the length of the array 110. Further a skirt 160 of more compliant polymer, such as silicone surrounds the array 110. FIG. 45 is a side view of the cochlear electrode array 110. The cochlear electrode array 110 includes a bottom polymer layer 170, metal traces 172 and a top polymer layer 176. Openings in the top polymer layer 176 define electrodes 174.

The cochlear electrode array 110 is made flat as shown in FIGS. 44 and 45. It is then thermoformed, as described earlier, into a spiral shape to approximate the shape of the cochlea, as shown in FIG. 46. The cochlear electrode array 110 is implanted with the bottom layer 170 formed toward the outside of the curvature, and the top polymer layer 176 toward the inside of the curvature. This curvature is opposite of the curvature resulting from the thermoforming process used for a retinal array 10. A cortical array would be thermoformed to curve inward like a cochlear array 110.

Figure 47A:
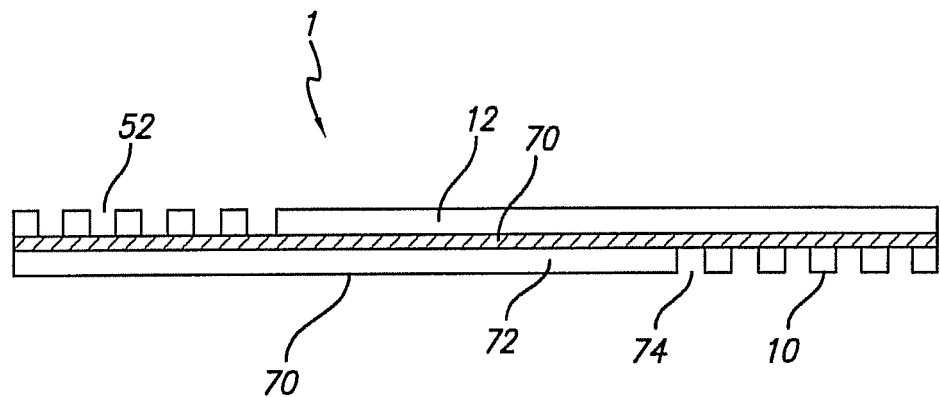
FIG. 47 shows a cross sectional view of an electrode array that is open on both sides.
Figure 47B:
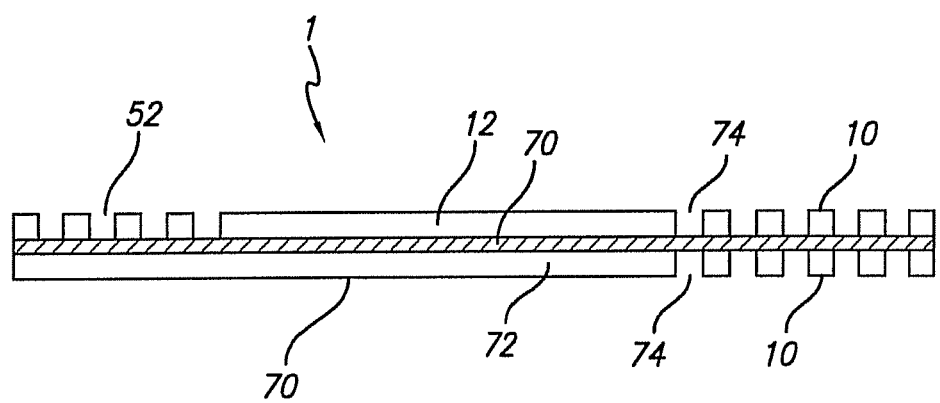

The present invention involves an electrode array device which is open on both sides of the polymer, as shown in FIGS. 47*a* and 47*b*. This device can be preferably obtained by a backside processing method. The purpose of backside processing of a polyimide device is to expose conductors on the other side of the polyimide device so that conductors on both sides are opened to meet special geometry requirement of the device.

FIG. 47*a* shows a cross sectional view of an electrode array device 1 that is open on both sides. Both sides of electrodes on an electrode array device 1 have to be open so that one side can be attached to retina and the other side to the bond pads of the electronic package.

FIG. 47*b* shows a cross sectional view of an electrode array device 1 that is open on both sides. The difference to the device as shown in FIG. 47*a* is that the device as shown in FIG. 47*b* includes electrod arrays 10 on both sides of the polymer 70.

Referring to FIG. 15, the flexible circuit electrode array device 1 is manufactured in layers. A base layer of polymer 70 is laid down, commonly by some form of chemical vapor deposition, spinning, meniscus coating or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIGS. 8-10). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. Alternatively, multiple alternating layers of metal and polymer may be applied to obtain more metal traces within a given width.

The invention involves methods to achieve a flexible electrode array having conductors on both sides of the polymer. The approaches underlined are designed so that the proposed processes are to be compatible with current thin film electrode array device 1 and thin film electrode array 10 like shown in FIG. 15. The process can be implemented as a clean process without introducing any undesirable residue or hazardous material. The backside processing leads to a flexible electrode array device 1 as shown in FIG. 47. The electrode array 10 with electrodes 74 and the bond pads 52 are located on opposite side of the flexible electrode cable 12. Each approach is an integral method by itself.

Embedded Mask Method

Figure 48:
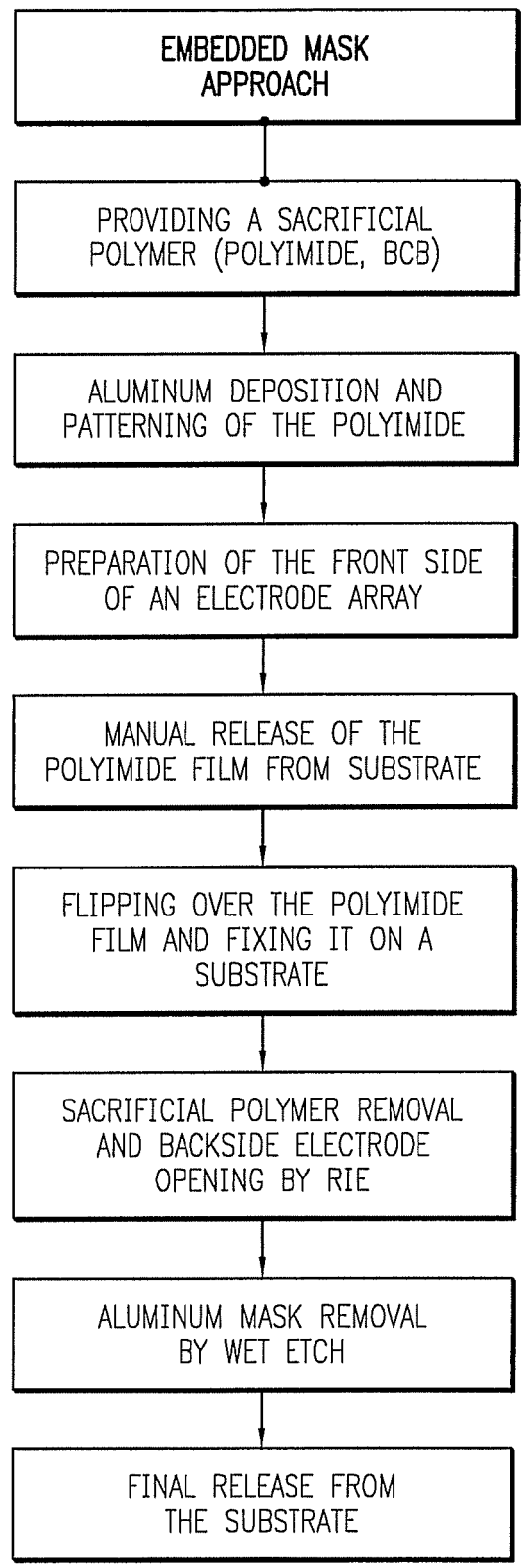
FIG. 48 shows a flow chart: the embedded mask method.

The process begins with a sacrificial layer of polymer (Polyimide or BCB) coated on glass. A layer of masking material with metal (Al, Ti etc.), preferably Al, semiconductor (Si) or ceramic material ($SiO_2$ or $Si_3N_4$) is then deposited on the polymer layer and patterned. When the polyimide film is flipped over after front side process is completed, the embedded mask acts as the mask to open the conductors on the opposite side as shown in FIG. 48 (embedded mask).

The embedded mask process involves preferably the following process steps:
Providing a sacrificial polymer (Polyimide, BCB) on a substrate;
Depositing Aluminum on the polymer and patterning the polyimide;
Preparing the front side of an electrode array to achieve a pattern like shown in FIG. 15;
Releasing the polyimide film manually from the substrate;
Flipping over the polyimide film and fixing the polyimide on the substrate;
Removing of polymer and backside electrode opening by RIE;
Removing the aluminum mask by wet etch; and
Releasing the electrode array from the substrate.

Thick Photoresist Method

Figure 49:
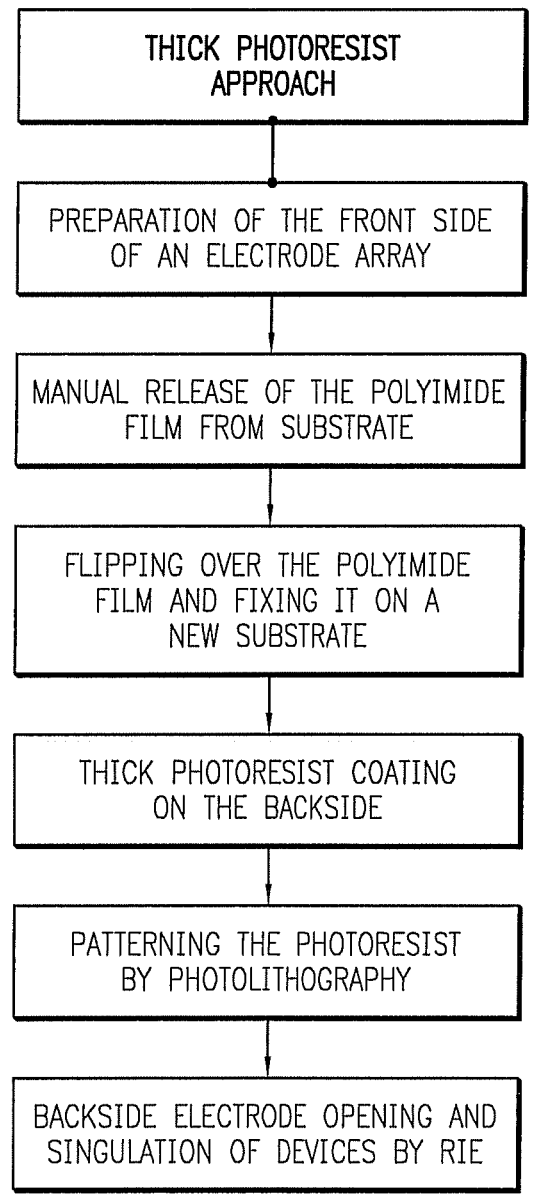
FIG. 49 shows a flow chart: the thick photoresist method.

Upon the completion of front side processes, polyimide film is cut, flipped and adhered on a clean wafer. Thick photoresist is coated and patterned and it acts as a sacrificial mask during RIE insulation via opening process. The photoresist has to be thick enough that a few micrometers thick of photoresist should remain on the polyimide surface after the RIE process, as shown in FIG. 49 (Thick Photoresist).

The thick photoresist process involves preferably the following process steps:
Preparing the front side of an electrode array to achieve a pattern like shown in FIG. 15;
Releasing the polyimide film manually from the substrate;
Flipping over the polyimide film and fixing the polyimide on a new substrate;
Coating thick photoresist on the backside of the polymer;
Patterning the photoresist by photolithography;
Opening backside electrodes by RIE; and
Singulation of devices by RIE.

The adherence of the polyimide film is achieved by water or iso-propanol surface tension during drying process in $N_2$ desiccators. The advantage of the adherence method over adhesives is that it is a clean process and does not introduce any foreign material residue. This way no releasing step is needed.

Another fixing method is achieved by spin-on silicone on some substrates as a carrier to transfer the polyimide film onto the silicone coated substrate. Polyimide film is then subjected to the thick photoresist process. There are two possible ways of transfer:

Lamination

Lamination means here releasing of the polyimide film from substrate by peeling it off, and then flipping the polyimide over and laminating the film carefully on the silicone surface.

No Lamination

The edges of polyimide film are delaminated from the substrate without removing the film from glass, and then covering the polyimide surface with a silicone coated substrate so that polyimide sticks to the silicone surface. The silicone coated substrate is preferably flexible and has adhesive on the back. The flexible substrate with the attached polyimide is peeled off from glass very gently and finally the adhesive side is attached to a rigid substrate.

Shadow Mask Method

Figure 50:
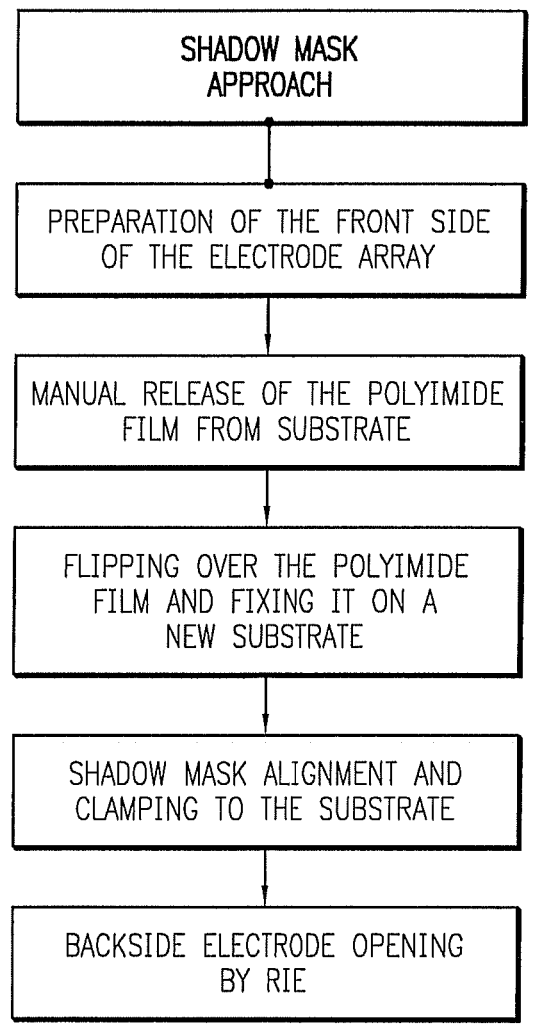
FIG. 50 shows a flow chart: the shadow mask method.

The invention involves the opening of the backside conductors using a rigid metal or silicon mask by aligning the mask to the flipped polyimide film and clamping the mask with the wafer using mechanical clamping mechanism, as shown in FIG. 50 (Shadow Mask).

The shadow mask process involves preferably the following process steps:
Preparing the front side of an electrode array to achieve a pattern like shown in FIG. 15;
Releasing the polyimide film manually from the substrate;
Flipping over the polyimide film and fixing the polyimide on a new substrate;
Aligning a shadow mask and clamping the polyimide to the substrate; and
opening backside electrodes by RIE.

Laser Opening Method

Figure 51:
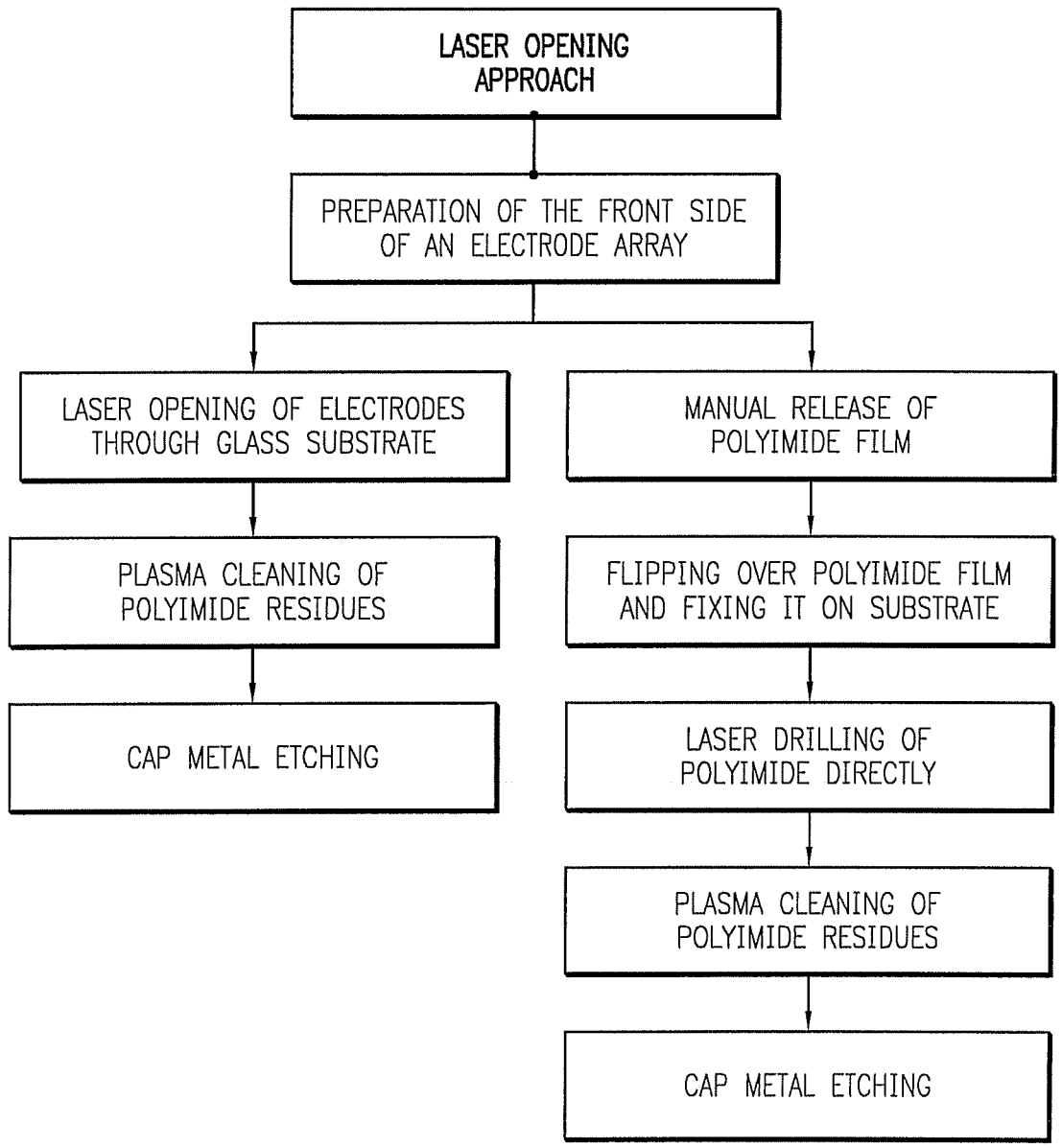
FIG. 51 shows a flow chart: laser opening method.

As UV or Excimer laser can penetrate and focus though glass. Laser ablation of polyimide on the backside (or bottom polyimide on glass) is applicable by using lasers without drilling the glass. The etching of polyimide can be selective to metal electrodes if the power density or other characteristics of laser and/or laser optics are optimized, as shown in FIG. 51 (Laser Opening).

The laser opening process involves preferably the following process steps:
Preparing the front side of an electrode array to achieve a pattern like shown in FIG. 15;
Releasing the polyimide film manually from the substrate;
Flipping over the polyimide film and fixing the polyimide on the substrate;
Drilling the polyimide directly by laser;
Cleaning of polyimide residues by plasma; and
Etching of cap metal.

The laser opening process involves alternatively preferably the following process steps:
Preparing the front side of an electrode array to achieve a pattern like shown in FIG. 15;
Opening of electrodes through glass substrate by laser;
Cleaning of polyimide residues by plasma; and Etching of cap metal.

Sacrificial Substrate with Backside Exposure Method

Figure 52:
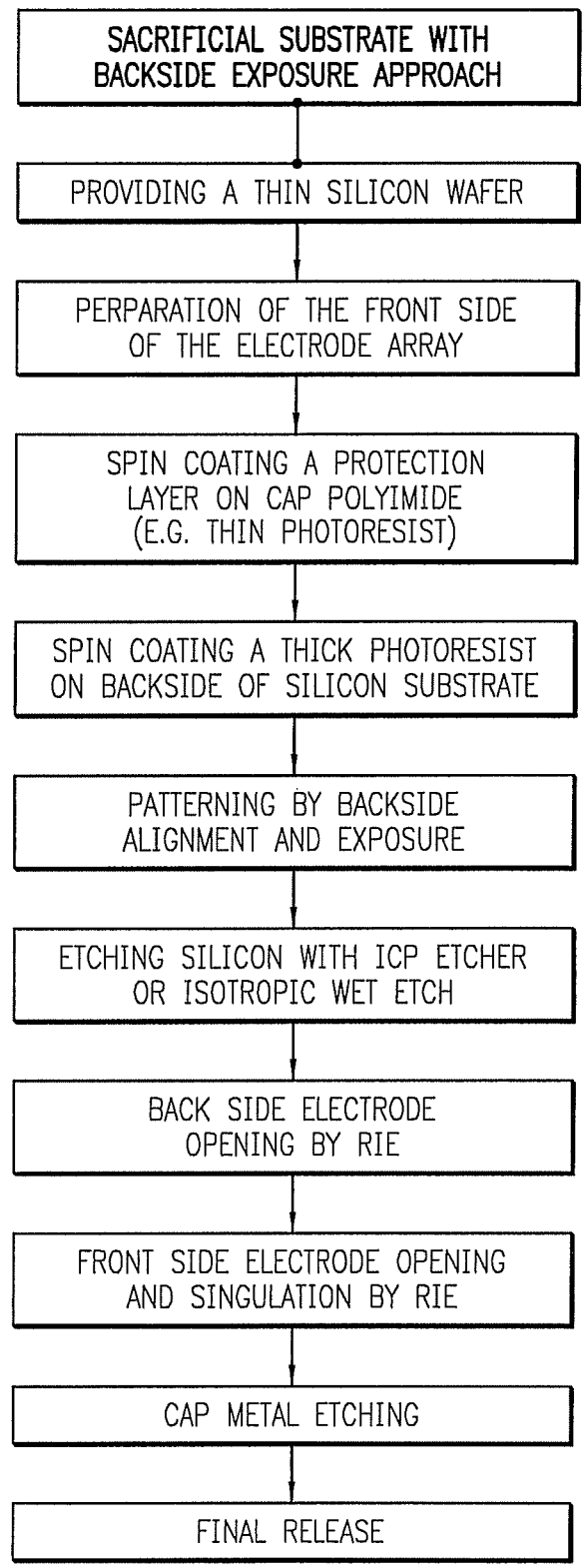
FIG. 52 shows a flow chart: substrate with backside exposure method.

When the front side process is completed, substrate (or carrier) is patterned and the backside conductors can be opened using the patterned substrate as a mask. The substrate material can be chosen from thin glass, silicon, silicon nitride or photo definable glass and other substrate material, as shown in FIG. 52 (Sacrificial Substrate with Backside Exposure).

The sacrificial substrate with backside exposure process involves preferably the following process steps:

Providing a thin silicon wafer;

Preparing the front side of an electrode array to achieve a pattern like shown in FIG. 15;

Spin coating a protection layer on cap polyimide (e.g. thin photoresist);

Spin coating a thick photoresist on backside of silicon substrate;

Patterning by backside alignment and exposure;

Etching Silicon with inductive coupling plasma (ICP) etcher or isotropic wet etch;

Backside electrode opening by RIE;

Front side electrode opening and singulation by RIE;

Etching of cap metal; and

Releasing the electrode array device.

Glass Wafer with Filled In Material

Figure 53:
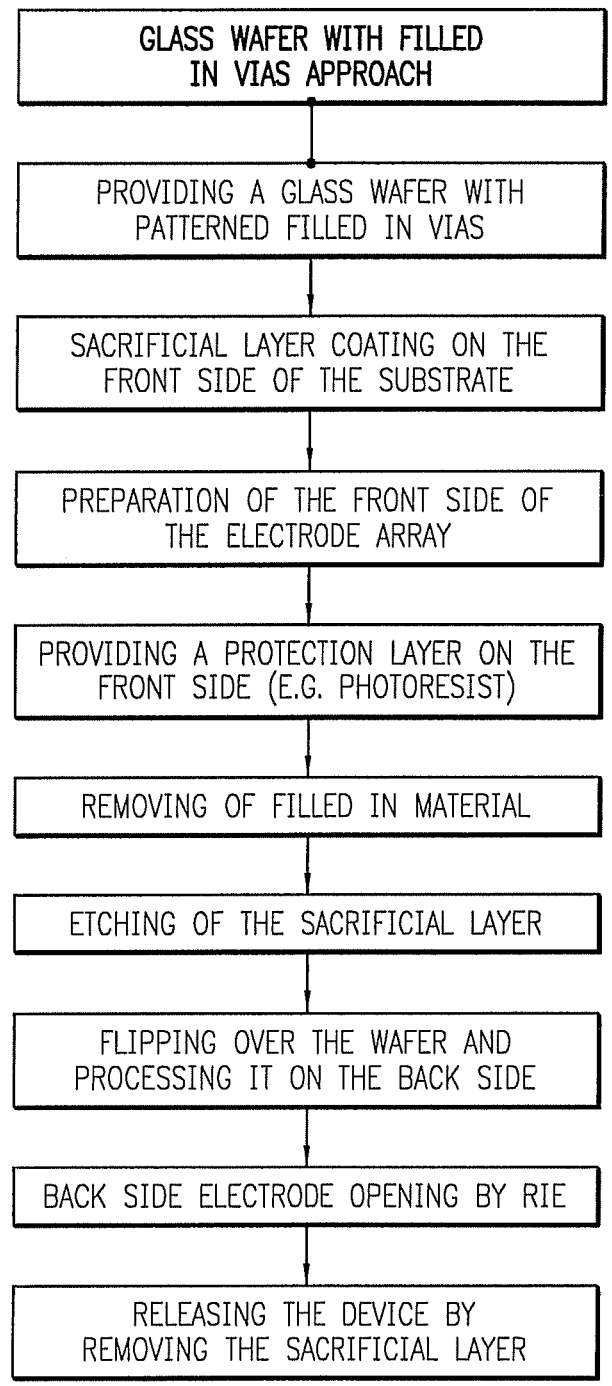
FIG. 53 shows a flow chart: glass wafer with filled in vias.

FIG. 53 shows a flow chart: glass wafer with filled in vias. A glass wafer with patterned bond pad vias is filled with sacrificial materials as substrate for front side processing. After the completion of the front side processing, the sacrificial material is removed in the vias and the back side bond pads are open with the patterned glass wafer as a mask.

The glass wafer with filled in vias process involves preferably the following process steps:

Providing a glass wafer with patterned filled in vias;

Providing a sacrificial layer coating on the front side of the substrate;

Preparing the front side of an electrode array to achieve a pattern like shown in FIG. 15;

Providing a protection layer on the front side (e.g. photoresist);

Removing of filled in material;

Etching of the sacrificial layer;

Flipping over the wafer and processing it on the back side;

Backside electrode opening by RIE; and

Releasing the device by removing the sacrificial layer.

Sacrificial materials filled in vias should be easily removed but should not be attacked by other chemicals that are used in the process. The following materials are used according to the present invention.

A layer of sacrificial adhesion layer including Ti and/or $TiO_2$ is coated on the front side of the glass before the front side process to improve the adhesion of polyimide on glass during the back side polyimide etching.

Photoresist and Aluminum mask protection is used on the front side polyimide during the back side processing.

Back side insulation via etch means opening the metal electrodes on the backside by removing polyimide material with Reactive Ion Etch (RIE).

Singulation of devices means etching with RIE process with prolonged time. A trench of polyimide material can be etched off from glass so that the arrays on a glass plate can be singulated (cut into individual arrays).

The two processes are performed at the same time with a patterned photoresist layer. The prolonged time in etch helps to remove the polyimide material having a thickness of approximately 10 μm from the surface of the glass, while the polyimide is approximately 5 μm thick on top of the metal layer and the openings are approximately 5 μm deep. This can be carried out because the RIE gas chemistry does not attack metal, only etches polyimide.

Accordingly, what has been shown is an improved method making a neural electrode array and improved method of stimulating neural tissue. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. An implantable device comprising:
   a flexible circuit including
      a polymer base layer, defining a void suitable to form an attachment point,
      patterned metal traces deposited on the polymer base layer forming electrodes in an electrode array suitable to contact neural tissue, bond pads and traces connecting the electrodes to bond pads, and
      a polymer top layer deposited on the polymer base layer and the metal traces; and
   an electronic package bonded to the bond pads;
   wherein the bond pads are located on the opposite side of the flexible circuit from the electrodes.

2. The implantable device according to claim 1, wherein the electrode array includes electrodes suitable to stimulate neural tissue.

3. The implantable device according to claim 1, wherein the polymer base layer contain polyimide, polyamide, LCP, Peek, polypropylene, polyethylene, paralyne, BCB or mixtures or copolymers or block copolymer thereof 4. The implantable device according to claim 1, wherein the traces contain Pt, Pd, Au, Ni, Ru, Ti, or alloys or layers thereof.

5. The implantable device according to claim 4, wherein the traces contain one or more layers.

6. The implantable device according to claim 1, wherein the electrodes contain Pt gray, Pt, Pd, Au, Ni, Ru, Ti, or alloys or layers thereof.

7. The implantable device according to claim 1, wherein the polymer base layer has a thickness of 2 μm to 4 μm.

8. The implantable device according to claim 1, wherein the electrode array is suitable to attach to retina and the bond pads are suitable to attach to bond pads of an electronic package.

9. The implantable device according to claim 1, wherein the electrodes comprise plated platinum grey.

10. The implantable device according to claim 1, wherein the bond pads comprise plated platinum grey.

11. The implantable device according to claim 1, wherein the polymer top layer defines voids at the electrodes.

12. The implantable device according to claim 1, wherein the polymer base layer defines voids at the bond pads.

13. The implantable device according to claim 1, further comprising a soft polymer, softer than the polymer base layer, covering at least part of the flexible circuit electrode array.

14. The implantable device according to claim 1, further comprising a stress relief surrounding the attachment point.

* * * * *